US009199972B2

(12) United States Patent
Parham et al.

(10) Patent No.: US 9,199,972 B2
(45) Date of Patent: Dec. 1, 2015

(54) MATERIALS FOR ORGANIC ELECTROLUMINESCENT DEVICES

(75) Inventors: Amir Hossain Parham, Frankfurt am Main (DE); Joachim Kaiser, Darmstadt (DE); Anja Gerhard, Egelsbach (DE); Jonas Valentin Kroeber, Frankfurt am Main (DE); Rémi Manouk Anémian, Seoul (KR)

(73) Assignee: Merck Patent GmbH (DE)

( * ) Notice: Subject to any disclaimer, the term of this patent is extended or adjusted under 35 U.S.C. 154(b) by 860 days.

(21) Appl. No.: 13/510,143

(22) PCT Filed: Oct. 28, 2010

(86) PCT No.: PCT/EP2010/006607
§ 371 (c)(1),
(2), (4) Date: May 16, 2012

(87) PCT Pub. No.: WO2011/060877
PCT Pub. Date: May 26, 2011

(65) Prior Publication Data
US 2012/0228552 A1  Sep. 13, 2012

(30) Foreign Application Priority Data

Nov. 17, 2009  (DE) .................. 10 2009 053 645

(51) Int. Cl.
| | | |
|---|---|---|
| H01L 51/50 | (2006.01) |
| C07D 403/10 | (2006.01) |
| C07D 403/14 | (2006.01) |
| C07D 471/04 | (2006.01) |
| C07D 487/04 | (2006.01) |
| C07D 519/00 | (2006.01) |
| C09K 11/06 | (2006.01) |
| H05B 33/14 | (2006.01) |
| C09B 57/00 | (2006.01) |
| C09B 57/10 | (2006.01) |
| H01L 51/00 | (2006.01) |

(52) U.S. Cl.
CPC ............ *C07D 403/10* (2013.01); *C07D 403/14* (2013.01); *C07D 471/04* (2013.01); *C07D 487/04* (2013.01); *C07D 519/00* (2013.01); *C09B 57/00* (2013.01); *C09B 57/10* (2013.01); *C09K 11/06* (2013.01); *H01L 51/0052* (2013.01); *H01L 51/0067* (2013.01); *H01L 51/0072* (2013.01); *H05B 33/14* (2013.01); *C09K 2211/1011* (2013.01); *C09K 2211/1029* (2013.01); *C09K 2211/1044* (2013.01); *C09K 2211/1059* (2013.01); *H01L 51/0008* (2013.01); *H01L 51/0077* (2013.01); *H01L 51/5016* (2013.01); *Y02E 10/549* (2013.01)

(58) Field of Classification Search
None
See application file for complete search history.

(56) References Cited

U.S. PATENT DOCUMENTS

| | | | |
|---|---|---|---|
| 8,003,227 B2 | 8/2011 | Vestweber et al. | |
| 8,614,357 B2 | 12/2013 | Bagala'Rampazzo et al. | |
| 8,653,537 B2 | 2/2014 | He et al. | |
| 8,679,647 B2 | 3/2014 | Pflumm et al. | |
| 8,859,111 B2 | 10/2014 | Parham et al. | |
| 2002/0034659 A1 | 3/2002 | Nishi et al. | |
| 2003/0111107 A1 | 6/2003 | Salbeck et al. | |
| 2006/0063027 A1 | 3/2006 | Vestweber et al. | |
| 2007/0051944 A1* | 3/2007 | Vestweber et al. | 257/40 |
| 2007/0144390 A1 | 6/2007 | Fejfar et al. | |
| 2011/0121274 A1 | 5/2011 | Parham et al. | |
| 2012/0056171 A1* | 3/2012 | Kim et al. | 257/40 |

FOREIGN PATENT DOCUMENTS

| | | |
|---|---|---|
| CN | 1954446 A | 4/2007 |
| CN | 101300214 A | 11/2008 |
| EP | 0968175 A1 | 1/2000 |
| JP | 2001-093670 A | 4/2001 |
| JP | 2001-518913 A | 10/2001 |
| JP | 2002-075645 A | 3/2002 |
| JP | 2004-083483 A | 3/2004 |
| JP | 2006-511939 A | 4/2006 |
| JP | 2006-131782 A | 5/2006 |
| JP | 2006-131783 A | 5/2006 |
| JP | 2007-049055 A | 2/2007 |
| JP | 2006-520875 A | 7/2007 |
| JP | 2008-509565 A | 3/2008 |
| JP | 2009-123976 A | 6/2009 |
| JP | 2009-266927 A | 11/2009 |
| JP | 2011-530802 A | 12/2011 |
| JP | 2012-513668 A | 6/2012 |
| JP | 2012-532902 A | 12/2012 |
| WO | WO-98/42655 A1 | 10/1998 |
| WO | WO-2004020373 A1 | 3/2004 |
| WO | WO-2004/058911 A2 | 7/2004 |

(Continued)

OTHER PUBLICATIONS

Natera, Jose, et al., "Synthesis and Properties of a Novel Cross-Linked Electroactive Polymer Formed from a Bipolar Starburst Monomer", Macromolecules, vol. 42, (2009), pp. 626-635.

Shen, Jiun Yi, et al., "High $T_g$ Blue Emitting Materials for Electroluminescent Devices", Journal of Materials Chemistry, vol. 15, (2005), pp. 2455-2463.

Spehr, Till, et al., "Highly Efficient Light Emitters Based on the Spiro Concept", Organic Electronics, vol. 4, (2003), pp. 61-69.

(Continued)

*Primary Examiner* — Gregory Clark
(74) *Attorney, Agent, or Firm* — Drinker Biddle & Reath LLP

(57) ABSTRACT

The present invention relates to organic electroluminescent devices which comprise fluorene derivatives and spiro ¬ bifluorene derivatives as matrix material for phosphorescent emitters.

20 Claims, No Drawings

(56) References Cited

FOREIGN PATENT DOCUMENTS

| WO | WO-2005/053055 A1 | 6/2005 |
| WO | WO-2006/005627 A1 | 1/2006 |

OTHER PUBLICATIONS

International Search Report for PCT/EP2010/006607 mailed Jan. 18, 2012.

Chinese Office Action dated Dec. 23, 2014 for Chinese Application No. 201080051831.1.

Pudaich et al., "Spiro Compounds for Organic Electroluminescence and Related Applications", *Adv. Polym. Sci.*, vol. 199, pp. 83-142 (2006).

Japanese Office Action mailed on Aug. 25, 2015 for Japanese Application No. 2012-539213.

\* cited by examiner

MATERIALS FOR ORGANIC ELECTROLUMINESCENT DEVICES

CROSS-REFERENCE TO RELATED APPLICATIONS

This application is a national stage application (under 35 U.S.C. §371) of PCT/EP2010/006607, filed Oct. 28, 2010, which claims benefit of German Application 10 2009 053 645.0, filed Nov. 17, 2009.

The present invention relates to materials for organic electroluminescent devices and to organic electroluminescent devices, in particular phosphorescent organic electroluminescent devices, which comprise fluorene derivatives and spirobifluorene derivatives as matrix materials.

Organic semiconductors are being developed for a number of different electronic applications. The structure of organic electroluminescent devices (OLEDs) in which these organic semiconductors are employed as functional materials is described, for example, in U.S. Pat. Nos. 4,539,507, 5,151, 629, EP 0676461 and WO 98/27136. However, further improvements are still necessary. Thus, there is still a need for improvement, in particular, with respect to the lifetime, efficiency and operating voltage of organic electroluminescent devices. It is furthermore necessary for the compounds to have high thermal stability and a high glass-transition temperature and to be sublimable without decomposition.

In particular, improvements in the properties are still necessary in the case of the electron-transport materials, since it is also precisely the properties of the electron-transport material that exert a significant influence on the above-mentioned properties of the organic electroluminescent device. In particular, there is a need for improvement in the case of electron-transport materials which simultaneously result in good efficiency, a long lifetime and a low operating voltage. It is also precisely the properties of the electron-transport material that are frequently limiting for the lifetime, efficiency and operating voltage of the organic electroluminescent device.

It would be desirable here to have available electron-transport materials which result in better electron injection into the emitting layer, since an electron-richer emission layer results in better efficiency. In addition, better injection enables the operating voltage to be reduced. Further improvements in the electron-transport material are therefore necessary for this purpose.

Furthermore, there is still generally a need for improvement in the processability of the materials, since many materials used in accordance with the prior art in organic electroluminescent devices tend to crystallise on the vapour-deposition source in the electroluminescent device production process and thus clog the vapour-deposition source during operation. It is therefore only with increased technical complexity that these materials can be employed in mass production.

Electroluminescent devices which use $AlQ_3$ as electron-transport material have already been known for some time and were described as long ago as 1993 in U.S. Pat. No. 4,539,507. $AlQ_3$ has since then frequently been used as electron-transport material, but has a number of disadvantages: it cannot be applied by vapour deposition without leaving a residue, since it partially decomposes at the sublimation temperature, which represents a major problem, in particular for production plants. This has the consequence that the vapour-deposition sources must be repeatedly cleaned or changed. Furthermore, decomposition products of $AlQ_3$ enter the OLED, where they contribute to a shortened lifetime and reduced quantum efficiency and power efficiency. In addition, $AlQ_3$ has low electron mobility, which results in higher voltages and thus in lower power efficiency. In order to avoid short circuits in the display, it is desired to increase the layer thickness; this is not possible with $AlQ_3$ owing to the low charge-carrier mobility and the resultant increase in voltage. The charge-carrier mobility of other electron-transport materials (U.S. Pat. No. 4,539,507) is likewise too low to build up thicker layers therewith, the life-time of the OLED being even worse than in the case of the use of $AlQ_3$. The inherent colour (yellow in the solid state) of $AlQ_3$, which can result in colour shifts, particularly in the case of blue OLEDs, due to reabsorption and weak re-emission, also proves to be unfavourable. Blue OLEDs can only be produced here with considerable reductions in efficiency and adverse effects on colour location.

Thus, there continues to be a demand for electron-transport materials which result in good efficiencies and at the same time in long lifetimes in organic electroluminescent devices. It has now been found, surprisingly, that organic electroluminescent devices which comprise certain triazine derivatives, shown below, as electron-transport materials have significant improvements over the prior art. With these materials, it is possible simultaneously to obtain high efficiencies and long lifetimes, which is not possible with materials in accordance with the prior art. In addition, it has been found that the operating voltages can additionally be significantly reduced, which results in higher power efficiencies.

Improvements in the above-mentioned properties are also necessary in the case of phosphorescent electroluminescent devices. In particular, there is a need for improvement in the case of matrix materials for phosphorescent emitters which simultaneously result in good efficiency, a long lifetime and a low operating voltage. It is precisely the properties of the matrix materials that are frequently limiting for the lifetime and efficiency of the organic electroluminescent device.

In accordance with the prior art, carbazole derivatives, for example bis(carbazolyl)biphenyl, are frequently used as matrix materials. There is still a need for improvement here, in particular with respect to the lifetime and glass-transition temperature of the materials.

Furthermore, ketones (WO 04/093207), phosphine oxides and sulfones (WO 05/003253) are used as matrix materials for phosphorescent emitters. In particular with ketones, low operating voltages and long lifetimes are achieved. There is still a need for improvement here, in particular with respect to the efficiency and compatibility with metal complexes which contain ketoketonate ligands, for example acetylacetonate.

Furthermore, metal complexes, for example BAlq or bis[2-(2-benzothiazole)phenolato]zinc(II), are used as matrix materials for phosphorescent emitters. There is still a need for improvement here, in particular with respect to the operating voltage and chemical stability. Purely organic compounds are frequently more stable than these metal complexes. Thus, some of these metal complexes are hydrolysis-sensitive, which makes handling of the complexes more difficult.

In particular, there is still a need for an improvement in matrix materials for phosphorescent emitters which simultaneously result in high efficiencies, long lifetimes and low operating voltages and which are also compatible with phosphorescent emitters which carry ketoketonate ligands.

Surprisingly, it has been found that fluorene derivatives which are substituted by triazine or other electron-deficient nitrogen heterocycles and which are simultaneously substituted by carbazole or carbazole derivatives, in particular spirobifluorene derivatives, are very highly suitable as matrix materials for phosphorescent emitters and in this use result in OLEDs which simultaneously have high efficiencies, long lifetimes and low operating voltages, including with phosphorescent emitters which contain ketoketonate ligands.

U.S. Pat. Nos. 6,229,012 and 6,225,467 disclose the use of fluorene derivatives which are substituted by triazine groups as electron-transport material in OLEDs. However, the application does not reveal that these materials are also suitable as matrix materials for phosphorescent emitters.

WO 05/053055 discloses the use of triazine derivatives, in particular spirobifluorene derivatives which are substituted by triazine groups, as hole-blocking material in phosphorescent OLEDs. However, the application does not reveal that these materials are also suitable as matrix materials for phosphorescent emitters.

The invention relates to a compound of the formula (1), (2), (3a) or (3b),

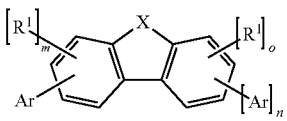

formula (1)

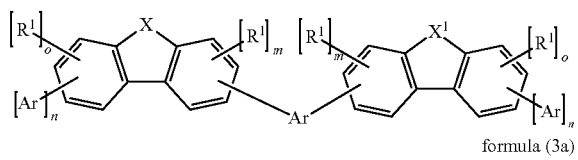

formula (2)

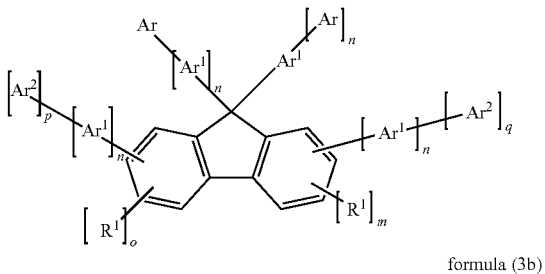

formula (3a)

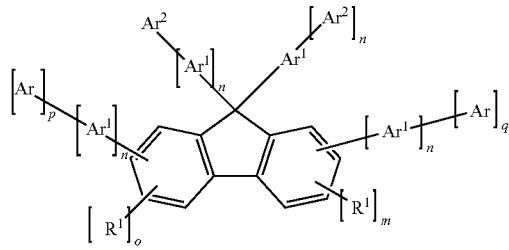

formula (3b)

where the following applies to the symbols and indices used:

Ar is on each occurrence, identically or differently, a heteroaryl group selected from the group consisting of triazine, pyrazine, pyrimidine, pyridazine, pyridine, pyrazole, imidazole, oxazole, 1,3,4-oxadiazole, benzimidazole and thiazole, each of which may be substituted by one or more groups $R^1$;

X is a group of the formula (4), where the dashed bond in each case indicates the bond to the two benzene rings:

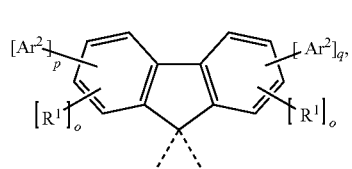

formula (4)

or X is on each occurrence, identically or differently, a divalent bridge selected from $B(Ar^2)$, $C(Ar^2)_2$, $C(Ar^1Ar^2)$, $Si(Ar^2)_2$, $C=C(Ar^2)_2$ or $C=NAr^2$;

$X^1$ is on each occurrence, identically or differently, X or a divalent bridge selected from $B(R^1)$, $C(R^1)_2$, $Si(R^1)_2$, $C=C(R^1)_2$, $C=NR^1$, $B(Ar^1)$, $C(Ar^1)_2$, $Si(Ar^1)_2$, $C=C(Ar^1)_2$ or $C=NAr^1$;

$R^1$ is on each occurrence, identically or differently, H, D, F, Cl, Br, I, CHO, $N(Ar^1)_2$, $C(=O)Ar^1$, $P(=O)(Ar^1)_2$, $S(=O)Ar^1$, $S(=O)_2Ar^1$, $CR^2=CR^2Ar^1$, CN, $NO_2$, $Si(R^2)_3$, $B(OR^2)_2$, $B(R^2)_2$, $B(N(R^2)_2)$, $OSO_2R^2$, a straight-chain alkyl, alkoxy or thioalkoxy group having 1 to 40 C atoms or a straight-chain alkenyl or alkynyl group having 2 to 40 C atoms or a branched or cyclic alkyl, alkenyl, alkynyl, alkoxy or thioalkoxy group having 3 to 40 C atoms, each of which may be substituted by one or more radicals $R^2$, where one or more, preferably non-adjacent $CH_2$ groups may be replaced by $R^2C=CR^2$, $C\equiv C$, $Si(R^2)_2$, $Ge(R^2)_2$, $Sn(R^2)_2$, $C=O$, $C=S$, $C=Se$, $C=NR^2$, $P(=O)(R^2)$, SO, $SO_2$, $NR^2$, O, S or $CONR^2$ and where one or more H atoms may be replaced by D, F, Cl, Br, I, CN or $NO_2$, or an aromatic or heteroaromatic ring system having 5 to 60 aromatic ring atoms, which may in each case be substituted by one or more radicals $R^2$, or an aryloxy or heteroaryloxy group having 5 to 60 aromatic ring atoms, which may be substituted by one or more radicals $R^2$, or an aralkyl or heteroaralkyl group having 5 to 60 aromatic ring atoms, which may be substituted by one or more radicals $R^2$; two or more adjacent substituents $R^1$ here may also form a mono- or polycyclic, aliphatic or aromatic ring system with one another;

$Ar^1$ is on each occurrence, identically or differently, an aromatic or heteroaromatic ring system having 5 to 30 aromatic ring atoms, which may be substituted by one or more radicals $R^2$; two radicals $Ar^1$ which are bonded to the same nitrogen, phosphorus or boron atom may here also be linked to one another by a single bond or a bridge selected from $B(R^2)$, $C(R^2)_2$, $Si(R^2)_2$, $C=O$, $C=NR^2$, $C=C(R^2)_2$, O, S, S=O, $SO_2$, $N(R^2)$, $P(R^2)$ and $P(=O)R^2$;

$R^2$ is on each occurrence, identically or differently, H, D or an aliphatic, aromatic and/or heteroaromatic organic radical, preferably a hydrocarbon radical having 1 to 20 C atoms, in which, in addition, H atoms may be replaced by D or F; two or more adjacent substituents $R^2$ here may also form a mono- or polycyclic, aliphatic or aromatic ring system with one another;

n is 0 or 1;
m is 0, 1, 2 or 3;
o is 0, 1, 2, 3 or 4 if m=0 and is 0, 1, 2 or 3 if m=1;
p, q are on each occurrence, identically or differently, 0 or 1, with the proviso that p+q is equal to 1 or 2;

where the compound of the formula (1), (2), (3a) or (3b) contains at least one group $Ar^2$, where $Ar^2$ is selected from a carbazole group, an azacarbazole group, a cis- or trans-indenocarbazole group, a cis- or trans-indenoazacarbazole group or a cis- or trans-indolocarbazole group, each of which may be substituted by one or more radicals $R^1$, where two or more adjacent substituents $R^1$, together with the atoms to which they are bonded, may also form a mono- or polycyclic, aliphatic or aromatic ring system with one another, with the proviso that the group $Ar^2$ is not in conjugation with the group Ar.

An aryl group in the sense of this invention contains at least 6 C atoms; a heteroaryl group in the sense of this invention contains at least 2 C atoms and at least 1 heteroatom, with the proviso that the sum of C atoms and heteroatoms is at least 5. The heteroatoms are preferably selected from N, O and/or S. An aryl group or heteroaryl group here is taken to mean either a simple aromatic ring, i.e. benzene, or a simple heteroaromatic ring, for example pyridine, pyrimidine, thiophene, etc., or a condensed aryl or heteroaryl group, for example naphthalene, anthracene, pyrene, quinoline, isoquinoline, etc.

An aromatic ring system in the sense of this invention contains at least 6 C atoms in the ring system. A heteroaromatic ring system in the sense of this invention contains at least 2 C atoms and at least one heteroatom in the ring system, with the proviso that the sum of C atoms and heteroatoms is at least 5. The heteroatoms are preferably selected from N, O and/or S. An aromatic or heteroaromatic ring system in the sense of this invention is intended to be taken to mean a system which does not necessarily contain only aryl or heteroaryl groups, but instead in which a plurality of aryl or heteroaryl groups may also be interrupted by a short non-aromatic unit (preferably less than 10% of the atoms other than H), such as, for example, an $sp^3$- or $sp^2$-hybridised C, N or O atom. Thus, for example, systems such as 9,9'-spirobifluorene, 9,9-diarylfluorene, triarylamine, diaryl ether, stilbene, benzophenone, etc., are also intended to be taken to be aromatic ring systems in the sense of this invention. Likewise, an aromatic or heteroaromatic ring system is taken to mean systems in which a plurality of aryl or heteroaryl groups are linked to one another by single bonds, for example biphenyl, terphenyl or bipyridine.

For the purposes of the present invention, an alkyl group having 1 to 40 C atoms, in which, in addition, individual H atoms or $CH_2$ groups may be substituted by the above-mentioned groups, is particularly preferably taken to mean the radicals methyl, ethyl, n-propyl, i-propyl, n-butyl, i-butyl, s-butyl, t-butyl, 2-methylbutyl, n-pentyl, s-pentyl, tert-pentyl, 2-pentyl, cyclopentyl, n-hexyl, s-hexyl, t-hexyl, 2-hexyl, 3-hexyl, cyclohexyl, 2-methylpentyl, n-heptyl, 2-heptyl, 3-heptyl, 4-heptyl, cycloheptyl, 1-methylcyclohexyl, n-octyl, 2-ethylhexyl, cyclooctyl, 1-bicyclo[2.2.2]octyl, 2-bicyclo[2.2.2]octyl, 2-(2,6-dimethyl)octyl, 3-(3,7-dimethyl)octyl, trifluoromethyl, pentafluoroethyl and 2,2,2-trifluoroethyl, and an alkenyl group is taken to mean, in particular, ethenyl, propenyl, butynyl, pentenyl, cyclopentenyl, hexenyl, cyclohexenyl, heptenyl, cycloheptenyl, octenyl and cyclooctenyl, and an alkynyl group is taken to mean, in particular, ethynyl, propynyl, butynyl, pentynyl, hexynyl, heptynyl or octynyl.

An alkoxy group having 1 to 40 C atoms is particularly preferably taken to mean methoxy, trifluoromethoxy, ethoxy, n-propoxy, i-propoxy, n-butoxy, i-butoxy, s-butoxy, t-butoxy or 2-methylbutoxy.

An aromatic or heteroaromatic ring system having 5-60 aromatic ring atoms, which may also in each case be substituted by the radicals R mentioned above and which may be linked to the aromatic or heteroaromatic group via any desired positions, is taken to mean, in particular, groups derived from benzene, naphthalene, anthracene, phenanthrene, benzanthracene, pyrene, chrysene, perylene, fluoranthene, benzofluoranthene, naphthacene, pentacene, benzopyrene, biphenyl, biphenylene, terphenyl, terphenylene, fluorene, benzofluorene, dibenzofluorene, spirobifluorene, dihydrophenanthrene, dihydropyrene, tetrahydropyrene, cis- or trans-indenofluorene, cis- or trans-monobenzoindenofluorene, cis- or trans-dibenzoindenofluorene, truxene, isotruxene, spirotruxene, spiroisotruxene, furan, benzofuran, isobenzofuran, dibenzofuran, thiophene, benzothiophene, isobenzothiophene, dibenzothiophene, pyrrole, indole, isoindole, carbazole, pyridine, quinoline, isoquinoline, acridine, phenanthridine, benzo-5,6-quinoline, benzo-6,7-quinoline, benzo-7,8-quinoline, phenothiazine, phenoxazine, pyrazole, indazole, imidazole, benzimidazole, naphthimidazole, phenanthrimidazole, pyridimidazole, pyrazinimidazole, quinoxalinimidazole, oxazole, benzoxazole, naphthoxazole, anthroxazole, phenanthroxazole, isoxazole, 1,2-thiazole, 1,3-thiazole, benzothiazole, pyridazine, benzopyridazine, pyrimidine, benzopyrimidine, quinoxaline, 1,5-diazaanthracene, 2,7-diazapyrene, 2,3-diazapyrene, 1,6-diazapyrene, 1,8-diazapyrene, 4,5-diazapyrene, 4,5,9,10-tetraazaperylene, pyrazine, phenazine, phenoxazine, phenothiazine, fluorubin, naphthyridine, azacarbazole, benzocarboline, phenanthroline, 1,2,3-triazole, 1,2,4-triazole, benzotriazole, 1,2,3-oxadiazole, 1,2,4-oxadiazole, 1,2,5-oxadiazole, 1,3,4-oxadiazole, 1,2,3-thiadiazole, 1,2,4-thiadiazole, 1,2,5-thiadiazole, 1,3,4-thiadiazole, 1,3,5-triazine, 1,2,4-triazine, 1,2,3-triazine, tetrazole, 1,2,4,5-tetrazine, 1,2,3,4-tetrazine, 1,2,3,5-tetrazine, purine, pteridine, indolizine and benzothiadiazole.

The compounds of the formulae (1), (2), (3a) and (3b) preferably have a glass-transition temperature $T_G$ of greater than 70° C., particularly preferably greater than 90° C., very particularly preferably greater than 110° C.

According to a preferred embodiment of the invention, the following applies to the symbols and indices used in the compounds of the formulae (1), (2), (3a) and (3b):

Ar is on each occurrence, identically or differently, triazine, pyrimidine or pyrazine, in particular triazine, each of which may be substituted by one or more radicals $R^1$;

X is on each occurrence, identically or differently, a group of the formula (4), where the dashed bond in each case indicates the bond to the two benzene rings;

$X^1$ is, identically or differently on each occurrence, a divalent bridge selected from $C(R^1)_2$, $Si(R^1)_2$ or $C=C(R^1)_2$, preferably $C(R^1)_2$;

$R^1$ is on each occurrence, identically or differently, H, a straight-chain alkyl, alkoxy or thioalkoxy group having 1 to 8 C atoms or an aromaticor heteroaromatic ring system having 5 to 20 aromatic ring atoms, each of which may be substituted by one or more radicals $R^2$, or an aryloxy or heteroaryloxy group having 5 to 20 aromatic ring atoms, which may be substituted by one or more radicals $R^2$, or a combination of these systems; two or more adjacent substituents $R^1$ here may also form a mono- or polycyclic, aliphatic or aromatic ring system with one another;

$Ar^1$ is on each occurrence, identically or differently, an aromatic or heteroaromatic ring system having 5 to 20, preferably 5 to 10, aromatic ring atoms, which may be substituted by one or more radicals $R^2$;

$R^2$ is on each occurrence, identically or differently, H, D or an aliphatic, aromatic and/or heteroaromatic organic radical having 1 to 10 C atoms, preferably 1 to 6 C atoms, in which, in addition, H atoms may be replaced by F; two or more adjacent substituents $R^2$ here may also form a mono- or polycyclic, aliphatic or aromatic ring system with one another;

$Ar^2$ is on each occurrence selected from the group consisting of carbazole, azacarbazole, indenocarbazole and indolocarbazole, each of which may also be substituted by one or more radicals $R^1$.

In a further embodiment of the invention, the compound of the formula (1), (2), (3a) or (3b) is selected from compounds of the formulae (5) to (12),
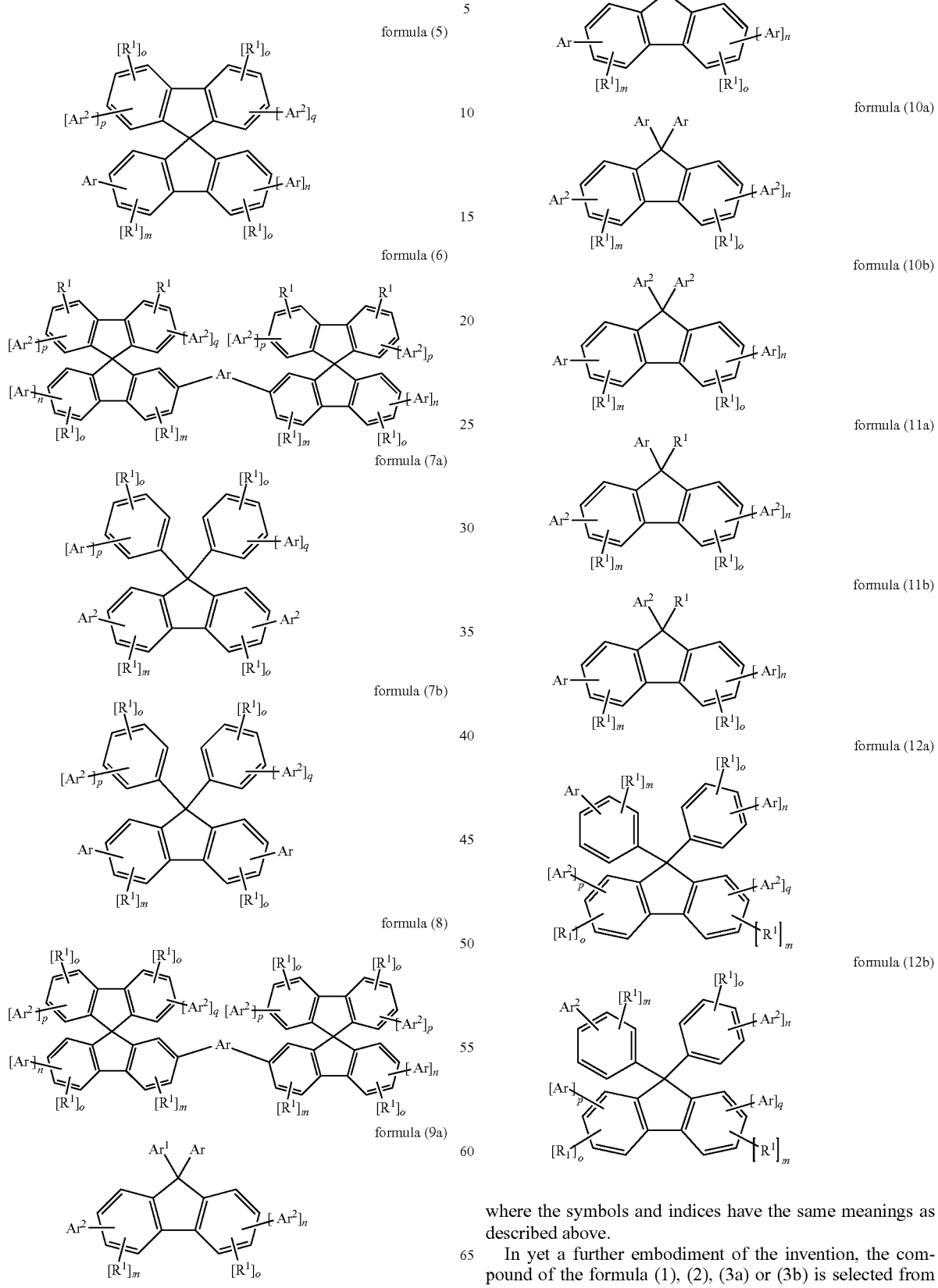
where the symbols and indices have the same meanings as described above.
In yet a further embodiment of the invention, the compound of the formula (1), (2), (3a) or (3b) is selected from compounds of the formulae (13) to (20),

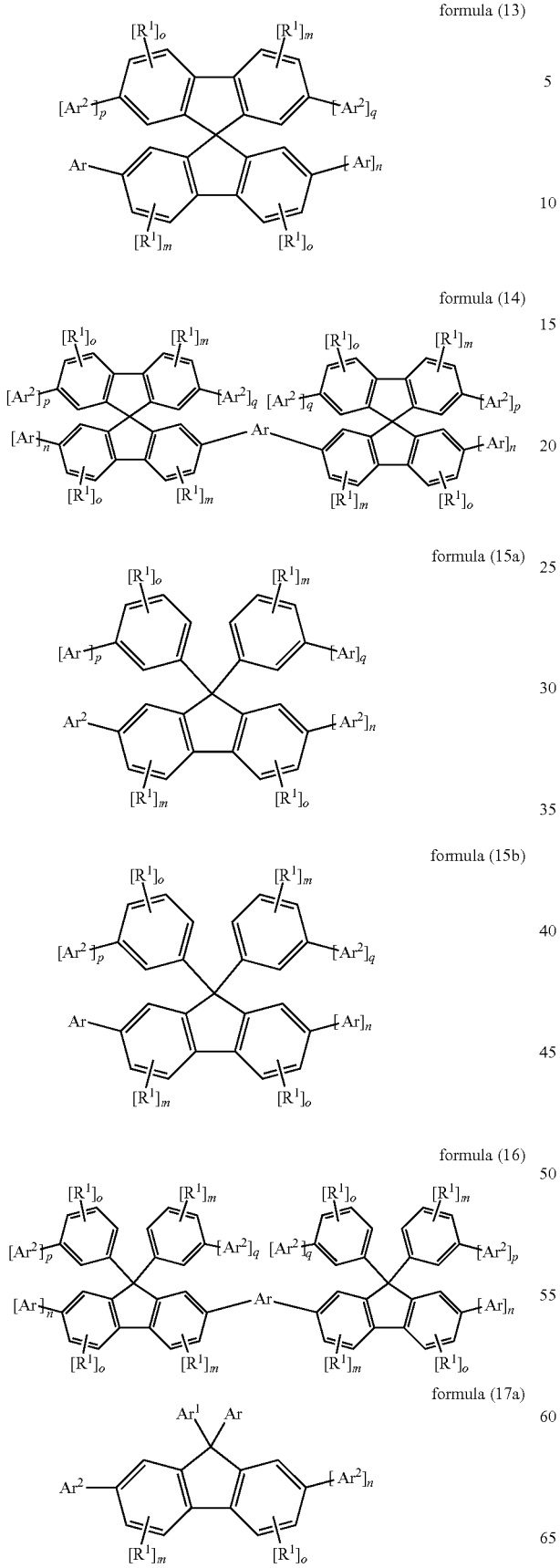
formula (13)
formula (14)
formula (15a)
formula (15b)
formula (16)
formula (17a)
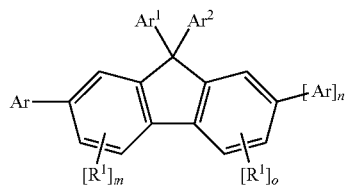
formula (17b)
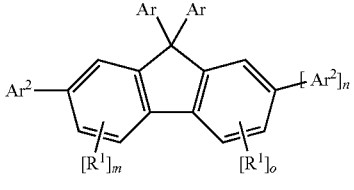
formula (18a)
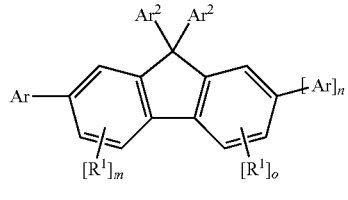
formula (18b)
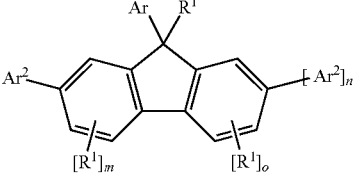
formula (19a)
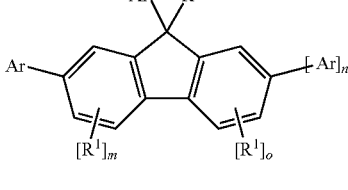
formula (19b)
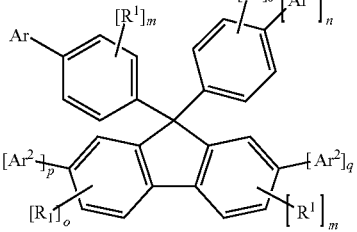
formula (20a)
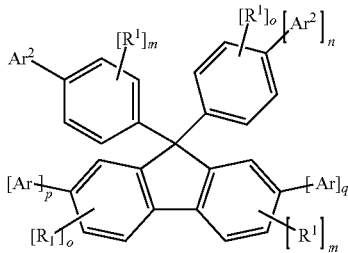
formula (20b)
where the symbols and indices have the meanings indicated above.
The compound of the formula (1), (2) or (3) is particularly preferably selected from compounds of the formulae (21) to (28), formula (21)
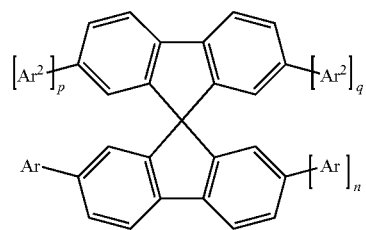

formula (22)
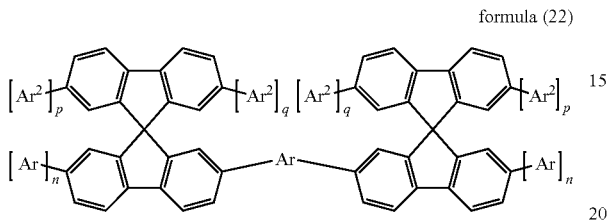

formula (23a)
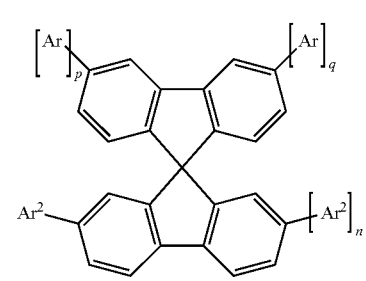

formula (23b)
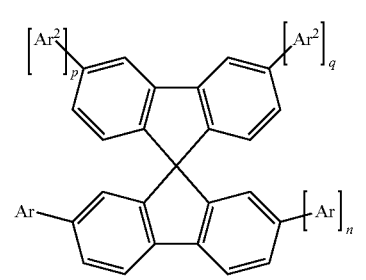

formula (24)
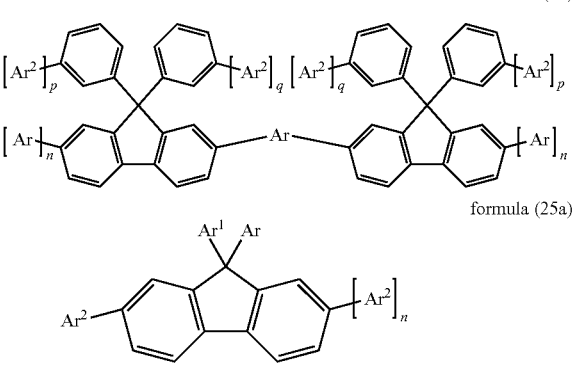

formula (25a)
formula (25b)
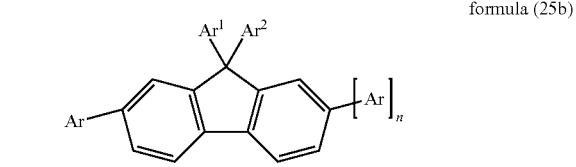

formula (26a)
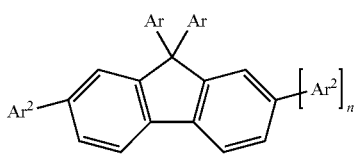

formula (26b)
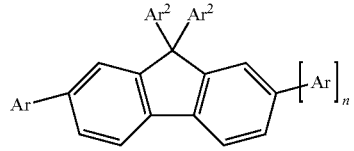

formula (27a)
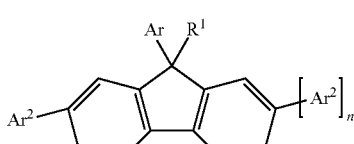

formula (27b)
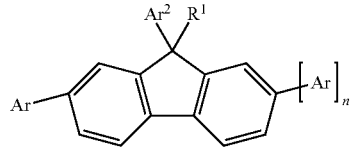

formula (28a)
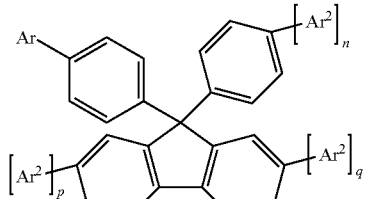

formula (28b)
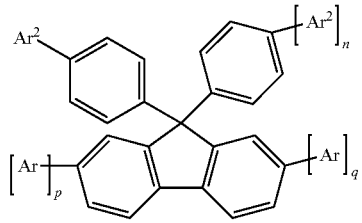

where the symbols and indices have the meanings indicated above. p and q here are on each occurrence, identically or differently, 0 or 1, where the sum of p and q is 1 or 2, and n is preferably 0 or 1.

The group Ar represents an electron-deficient heteroaromatic group. The group Ar preferably stands, identically or differently on each occurrence, for a 6-membered heteroaromatic ring, i.e. for triazine, pyrazine, pyrimidine, pyridazine or pyridine, each of which may be substituted by one or more radicals $R^1$.

In a preferred embodiment of the invention, the monovalent group Ar in compounds of the formulae (1), (3a) and (3b) is selected from the groups of the following formulae (29) to (41), where the dashed bond in each case indicates the bond from the group to the fluorene or spirobifluorene or, where appropriate, to $Ar^1$, and $R^1$ has the same meaning as described above:

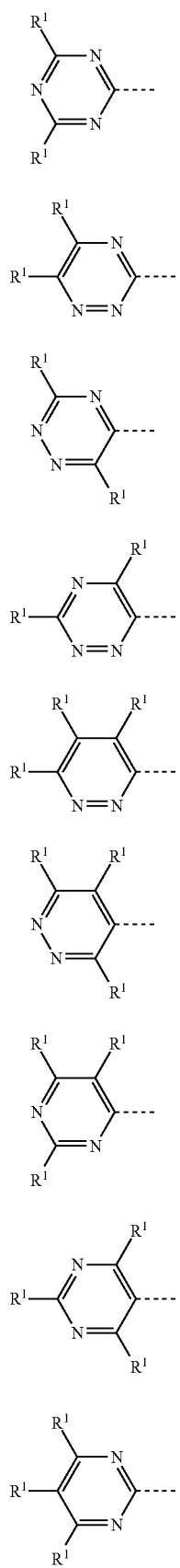

formula (29)
formula (30)
formula (31)
formula (32)
formula (33)
formula (34)
formula (35)
formula (36)
formula (37)

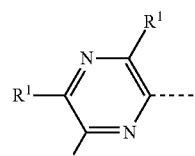

formula (38)

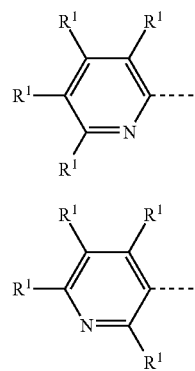

formula (39)

formula (40)

formula (41)

In a preferred embodiment of the invention, the divalent group Ar in compounds of the formula (2) is selected from the groups of the following formulae (42) to (49), where the dashed bonds in each case indicate the bond from the group to the fluorene or spirobifluorene, and $R^1$ has the same meaning as described above:

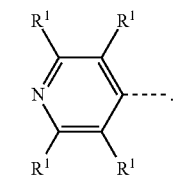

formula (42)

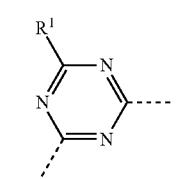

formula (43)

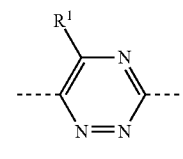

formula (44)

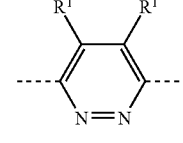

formula (45)

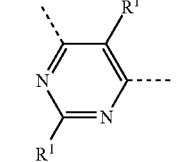

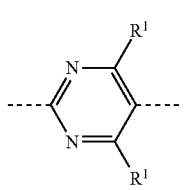

formula (46)

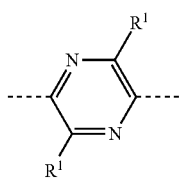

formula (47)

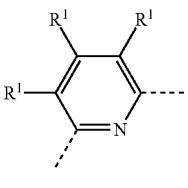

formula (48)

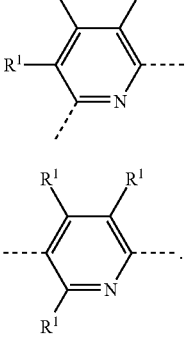

formula (49)

In a preferred embodiment of the invention, the group Ar contains two or three nitrogen atoms. Preferred monovalent groups Ar are therefore the groups of the formulae (29) to (38), and preferred divalent groups Ar are the groups of the formulae (42) to (47). The group Ar particularly preferably contains three nitrogen atoms. Particularly preferred monovalent groups Ar are therefore the groups of the formulae (29) to (32), in particular the group of the formula (29), and particularly preferred divalent groups Ar are the groups of the formulae (42) and (43), in particular the group of the formula (42).

In another preferred embodiment of the invention, the radical $R^1$ which is bonded to the groups of the formulae (29) to (49) stands, identically or differently on each occurrence, for H, D, a straight-chain alkyl or alkoxy group having 1 to 10, preferably 3 to 6, C atoms or a branched or cyclic alkyl or alkoxy group having 3 to 10, preferably 4 to 7, C atoms, each of which may be substituted by one or more radicals $R^2$, where one or more H atoms may be replaced by D or F, or an aromatic or heteroaromatic ring system having 5 to 30, preferably 6 to 15, aromatic ring atoms, which may in each case be substituted by one or more radicals $R^2$, or a combination of these systems. In a particularly preferred embodiment of the invention, the radical $R^1$ which is bonded to the groups of the formulae (29) to (49) stands, identically or differently on each occurrence, for H or D, a straight-chain alkyl group having 1 to 5 C atoms or a branched or cyclic alkyl group having 3 to 6 C atoms, each of which may be substituted by one or more radicals $R^2$, where one or more H atoms may be replaced by D or F, or for an aromatic or heteroaromatic ring system having 5 to 25 aromatic ring atoms, which may in each case be substituted by one or more radicals $R^2$, or a combination of these systems. The radical $R^1$ which is bonded to the groups of the formulae (29) to (49) very particularly preferably stands, identically or differently on each occurrence, for H or D or for an aromatic or heteroaromatic ring system having 5 to 14 aromatic ring atoms, which may in each case be substituted by one or more radicals $R^2$, in particular for phenyl, naphthyl or biphenyl, each of which may be substituted by one or more radicals $R^2$, but is preferably unsubstituted.

In another preferred embodiment of the invention, the radical $R^1$ which is bonded directly to the fluorene or spirobifluorene stands, identically or differently on each occurrence, for H, a straight-chain alkyl or alkoxy group having 1 to 10 C atoms or a branched or cyclic alkyl or alkoxy group having 3 to 10 C atoms, each of which may be substituted by one or more radicals $R^2$, where one or more H atoms may be replaced by D or F, or an aromatic or heteroaromatic ring system having 5 to 30 aromatic ring atoms, which may in each case be substituted by one or more radicals $R^2$, or a combination of these systems.

In a particularly preferred embodiment of the invention, the radical $R^1$ which is bonded directly to the fluorene or spirobifluorene stands, identically or differently on each occurrence, for H, a straight-chain alkyl group having 1 to 5 C atoms or a branched or cyclic alkyl group having 3 to 6 C atoms, each of which may be substituted by one or more radicals $R^2$, where one or more H atoms may be replaced by D or F, or for an aromatic or heteroaromatic ring system having 5 to 25 aromatic ring atoms, which may in each case be substituted by one or more radicals $R^2$.

In a further preferred embodiment of the invention, the group Ar is bonded in the 2-position of the fluorene or spirobifluorene or of the corresponding heterocycle. If more than one group Ar is present, the other groups Ar are preferably bonded in the 7-position and in spirobifluorene derivatives also in the 2'-position and 7'-position.

In a further preferred embodiment of the invention, the groups $Ar^2$ are selected from the following formulae (50) to (63), where the dashed bond in each case indicates the bonding of this group in the molecule, and the other symbols and indices used have the meanings given above:

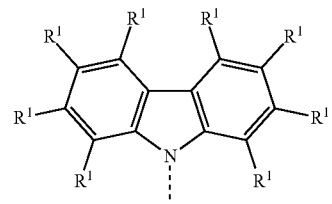

formula (50)

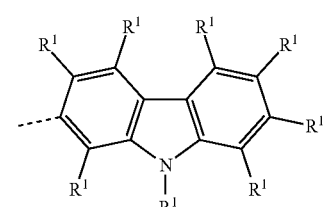

formula (51)

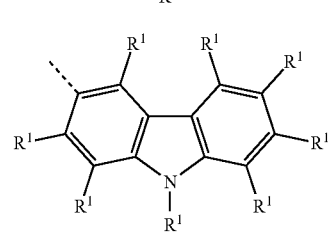

formula (52)

formula (53)
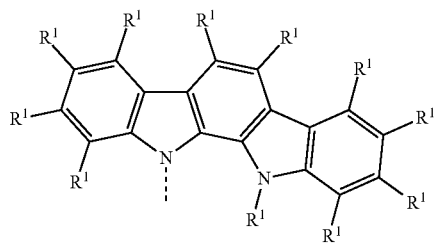
formula (54)
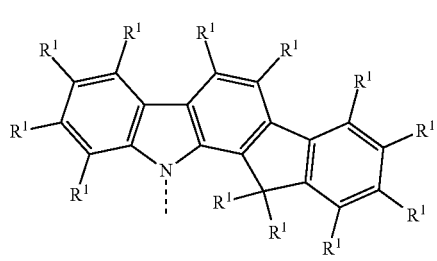
formula (55)
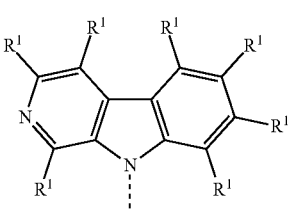
formula (56)
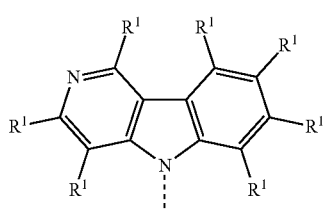
formula (57)
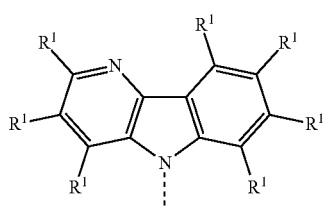
formula (58)
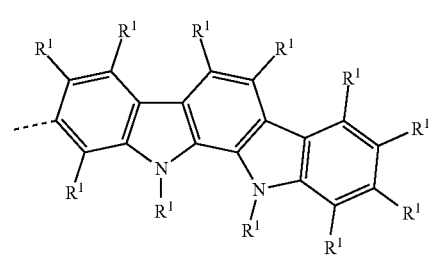
formula (59)
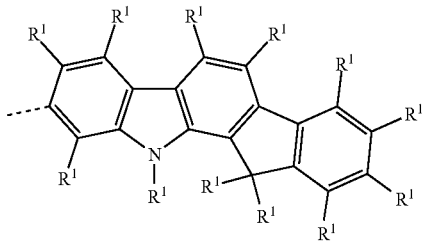
formula (60)
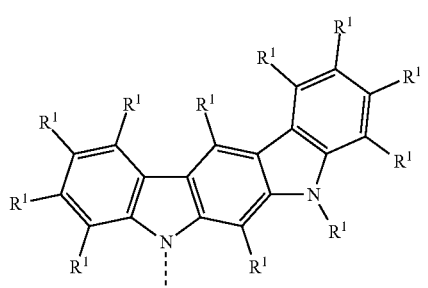
formula (61)
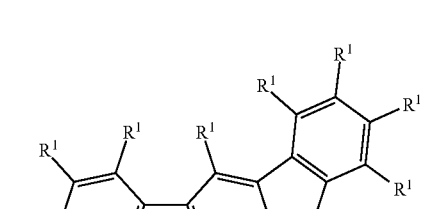
formula (62)
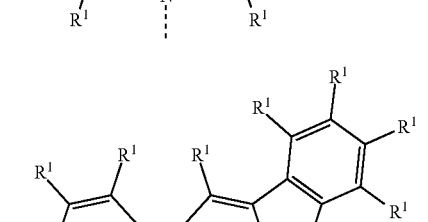
formula (63)
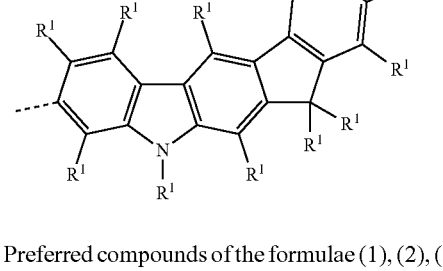
Preferred compounds of the formulae (1), (2), (3a) and (3b) are the compounds of the formulae (1-1) to (1-81).

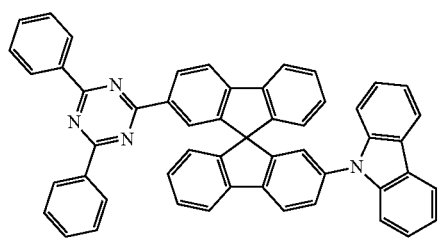 (1-1)
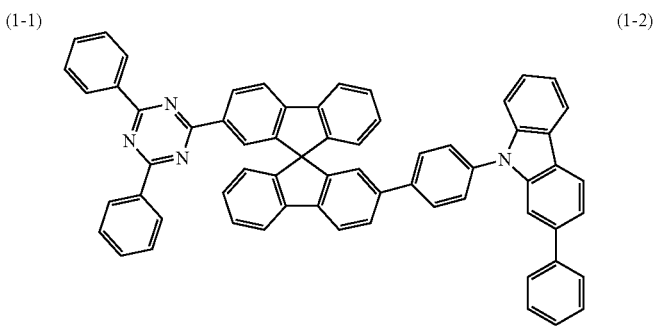 (1-2)
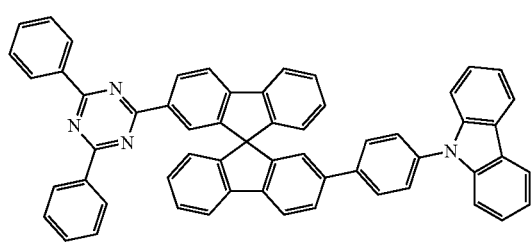 (1-3)
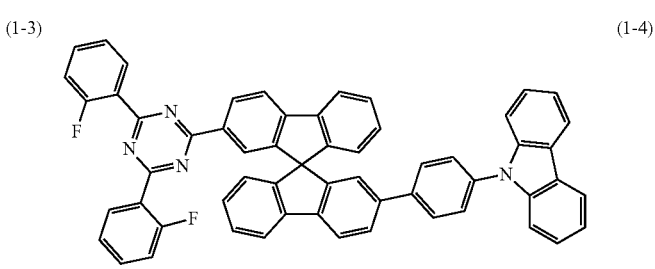 (1-4)
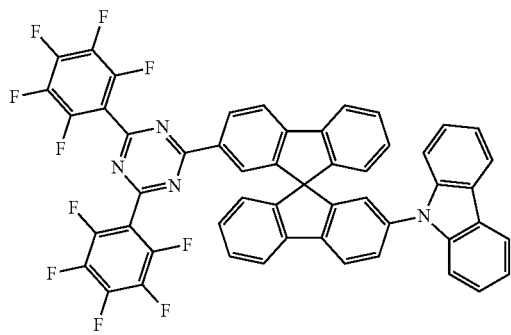 (1-5)
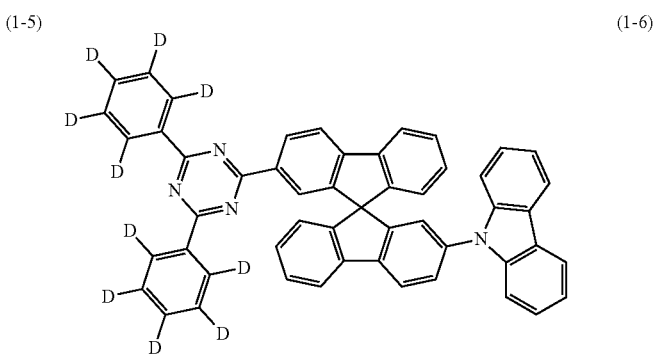 (1-6)
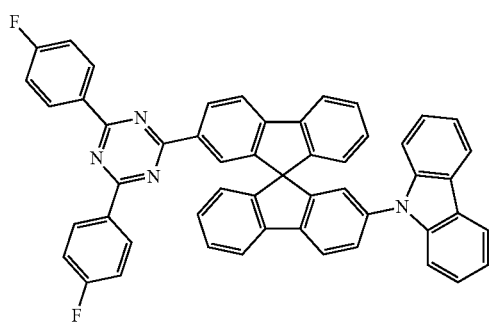 (1-7)
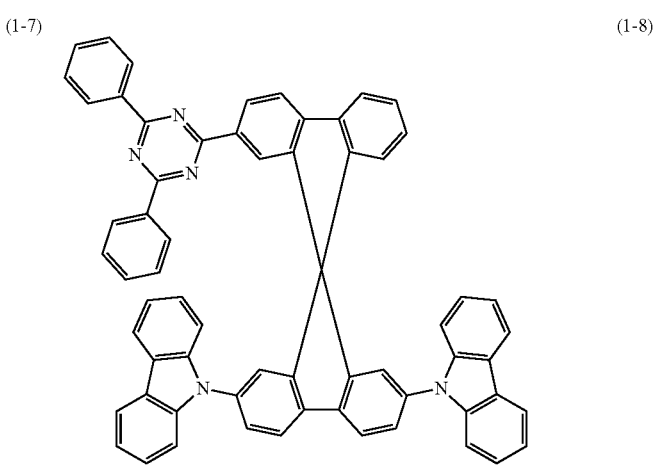 (1-8)

-continued
(1-9)
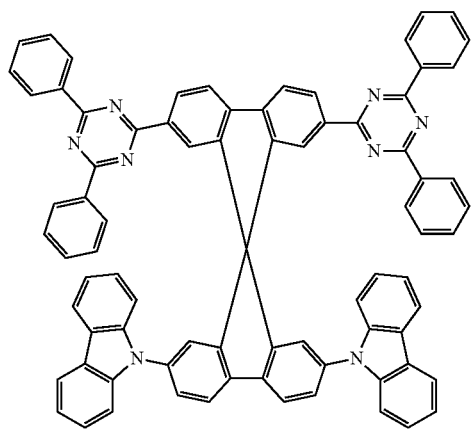
(1-10)
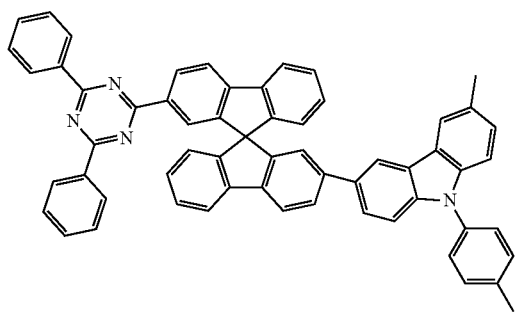
(1-11)
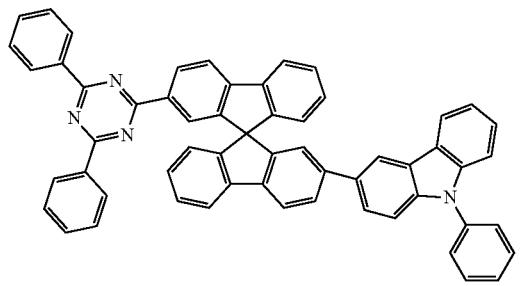
(1-12)
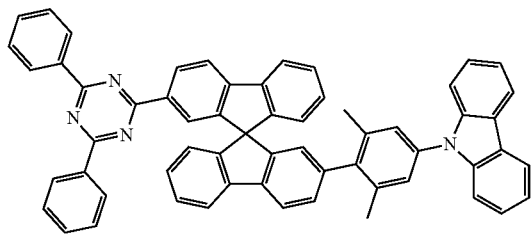
(1-13)
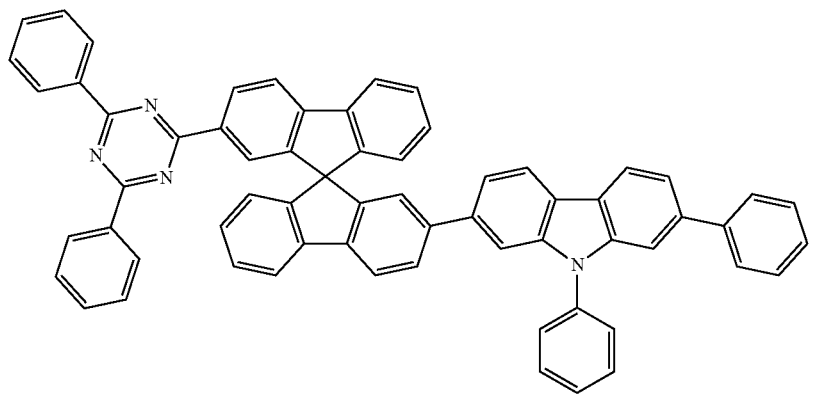
(1-14)
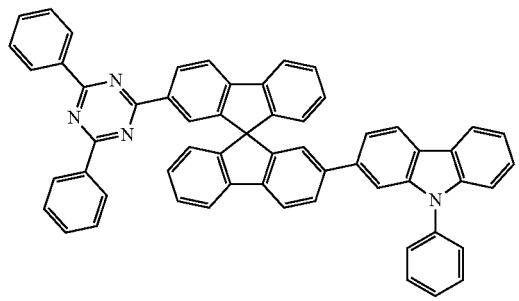
(1-15)
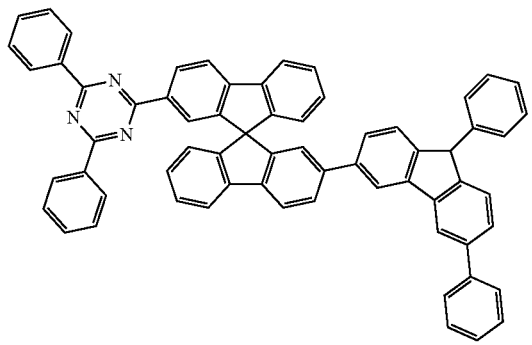

-continued
(1-16)
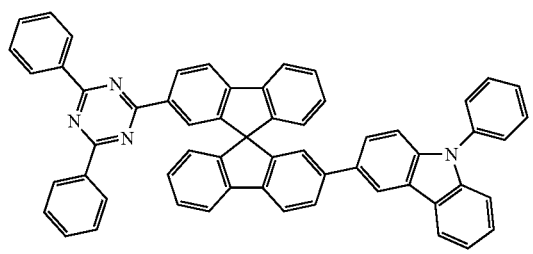
(1-17)
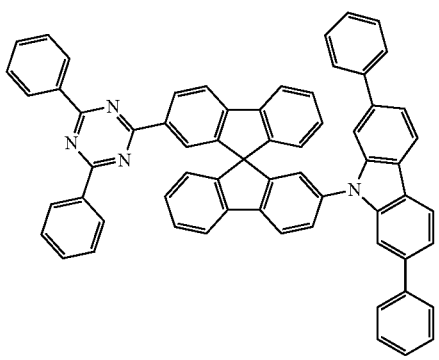
(1-18)
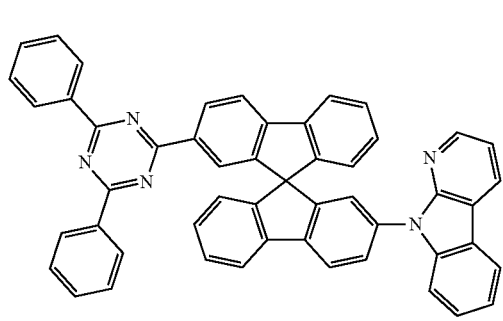
(1-19)
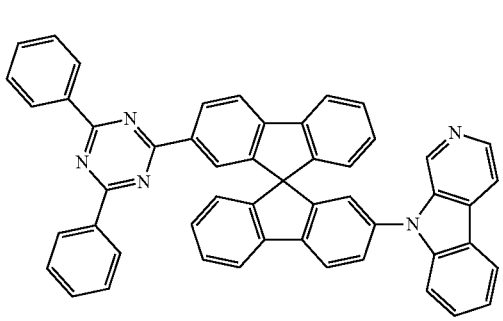
(1-20)
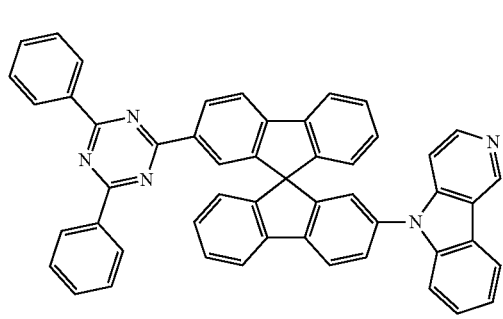
(1-21)
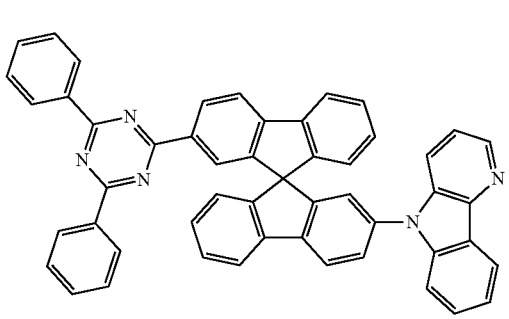
(1-22)
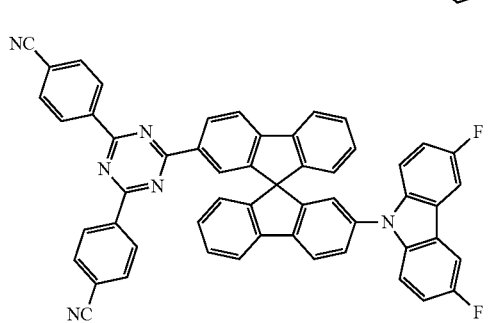
(1-23)
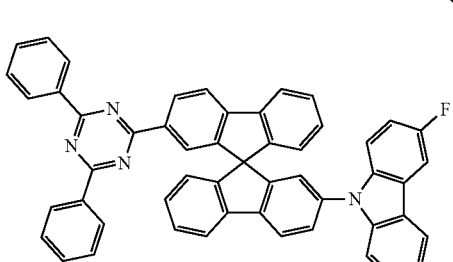
(1-24)
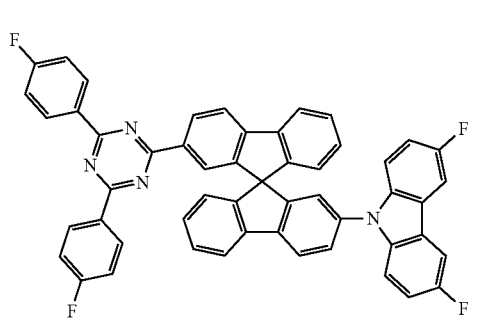
(1-25)
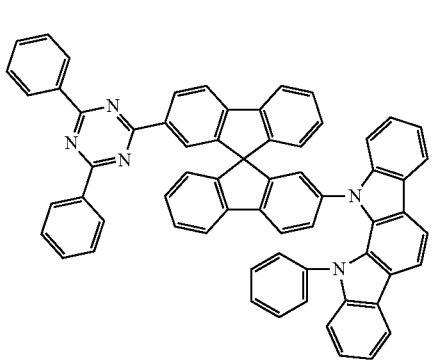

-continued
(1-26)
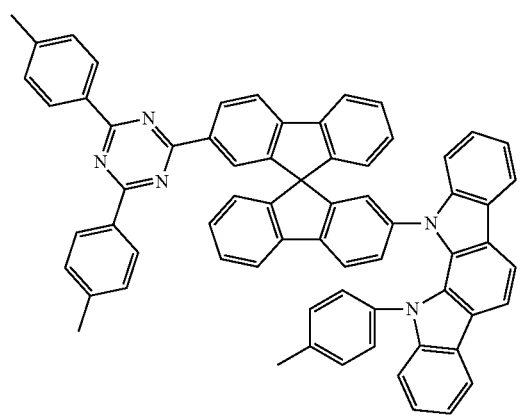
(1-27)
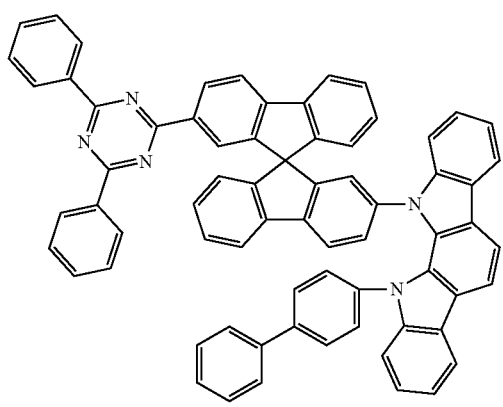
(1-28)
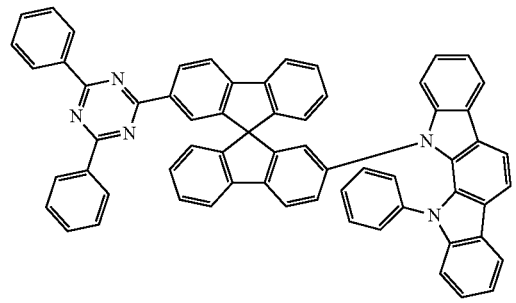
(1-29)
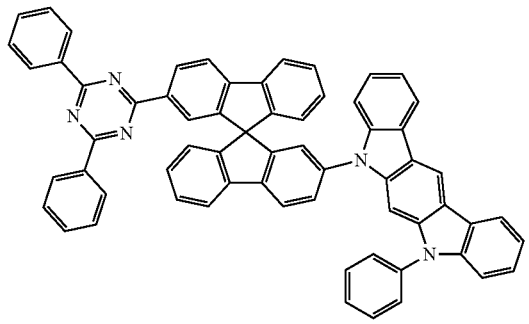
(1-30)
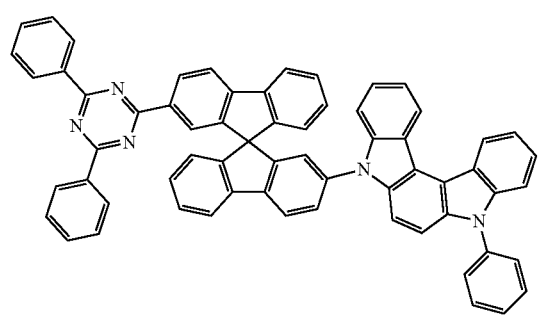
(1-31)
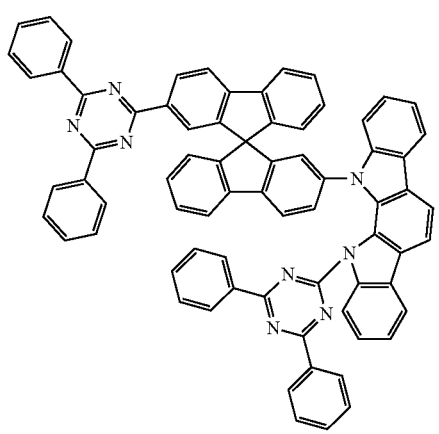

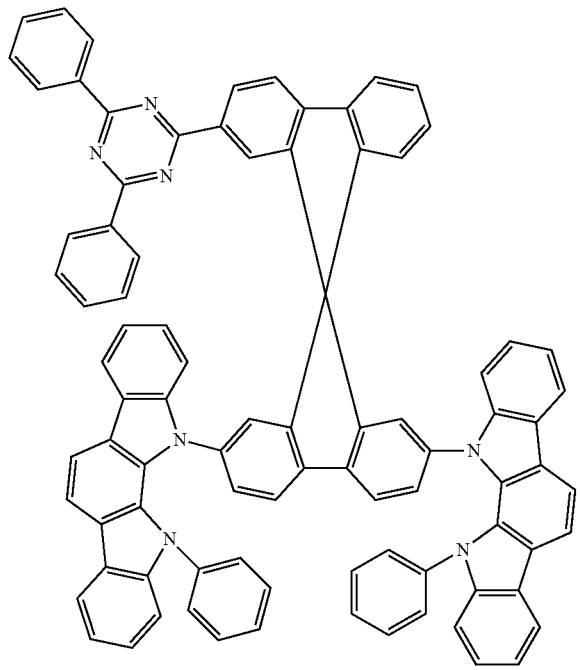
(1-32)
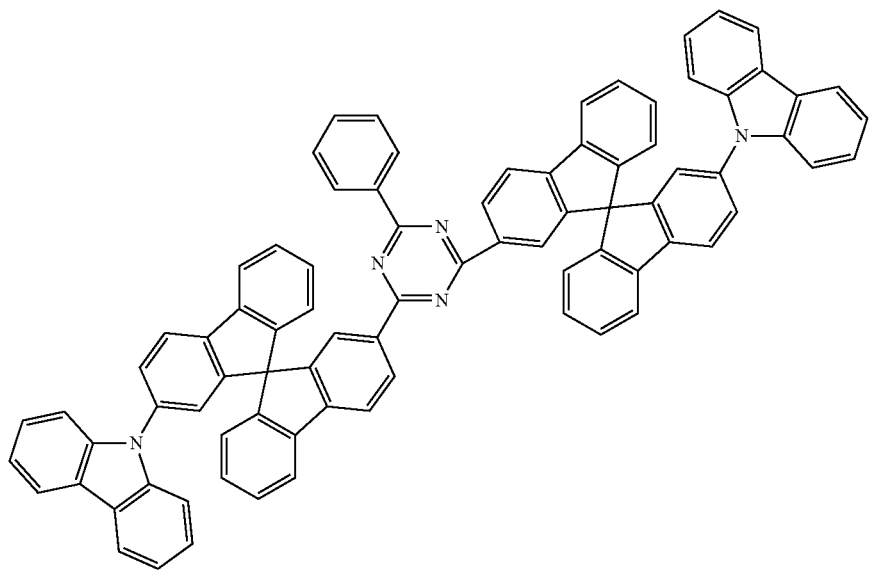
(1-33)
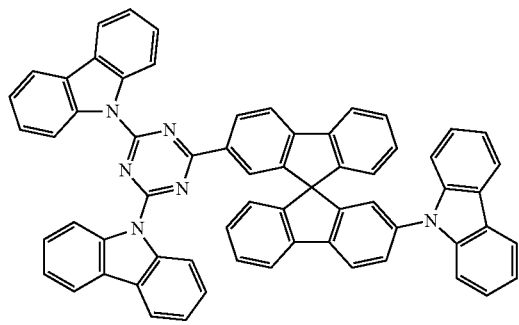
(1-34)
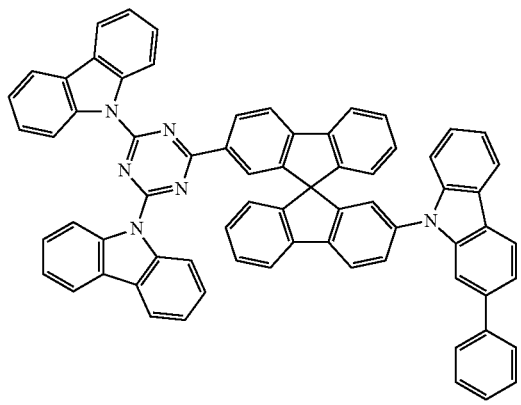
(1-35)

-continued
(1-36)
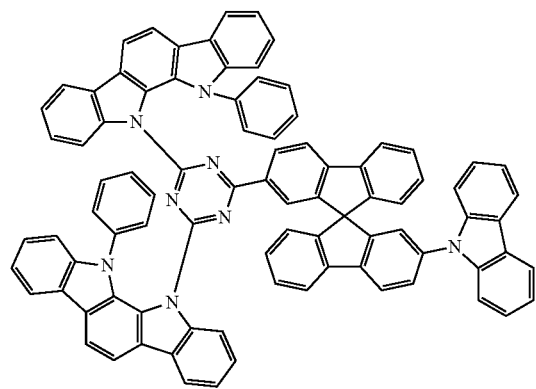
(1-37)
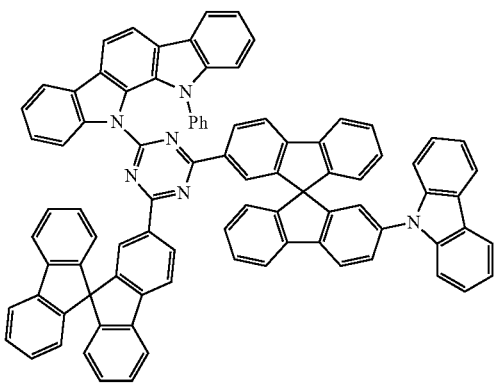
(1-38)
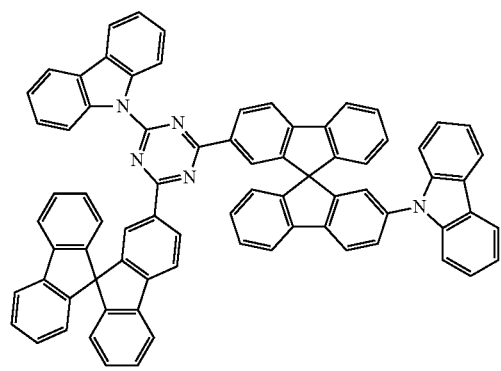
(1-39)
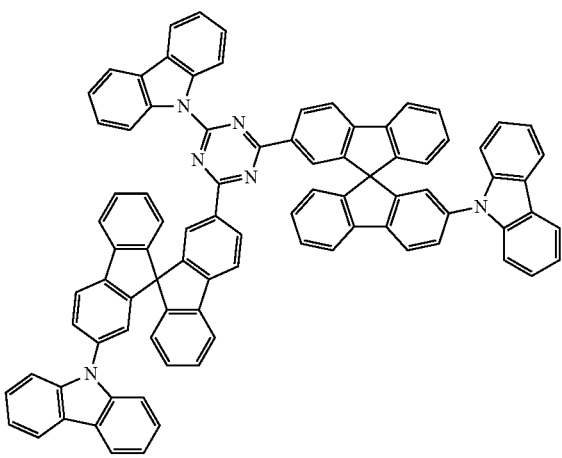
(1-40)
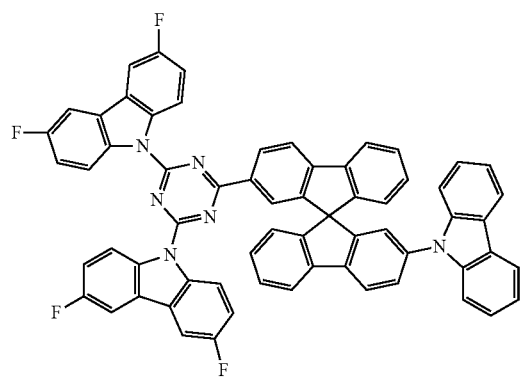
(1-41)
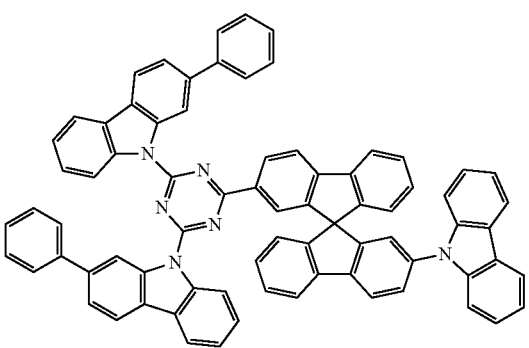

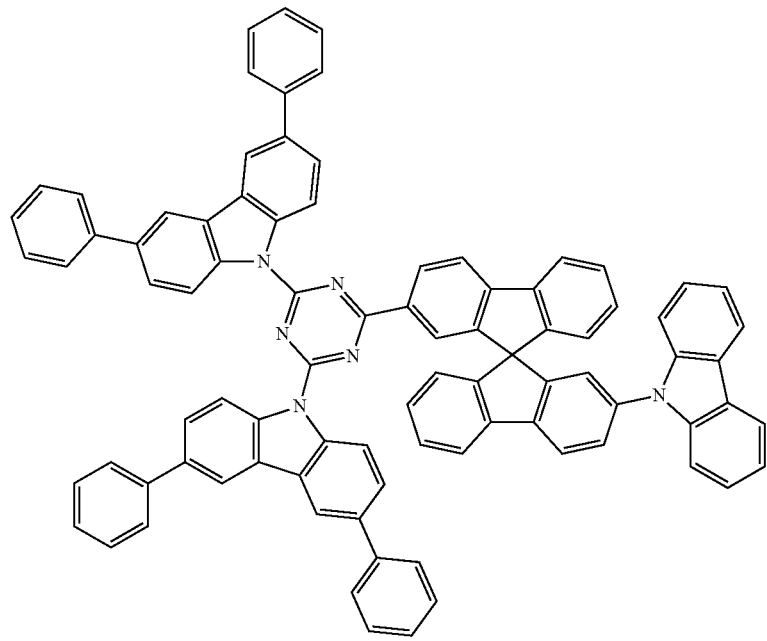
(1-42)
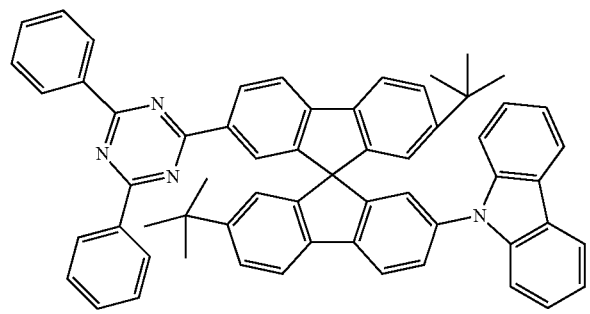
(1-43)
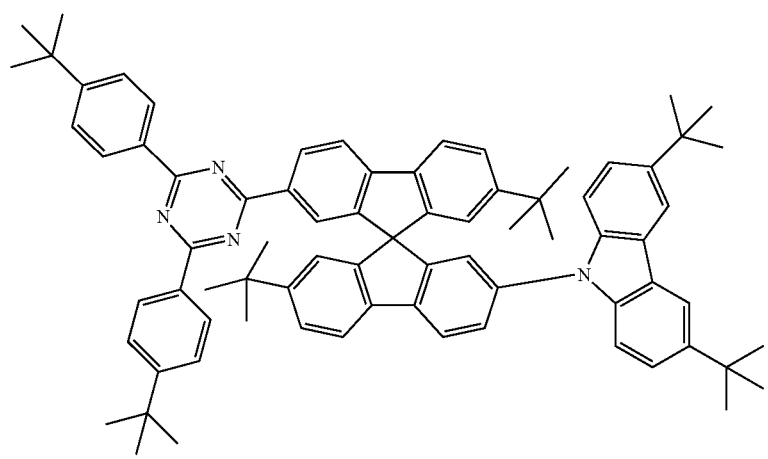
(1-44)

(1-45)
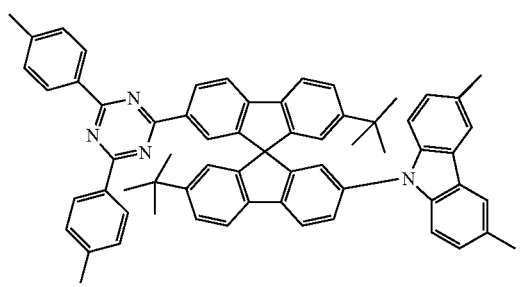
(1-46)
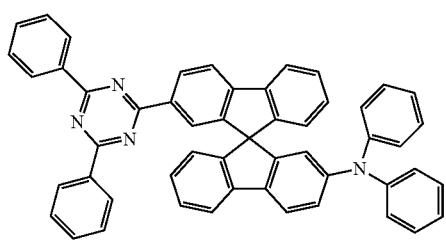
(1-47)
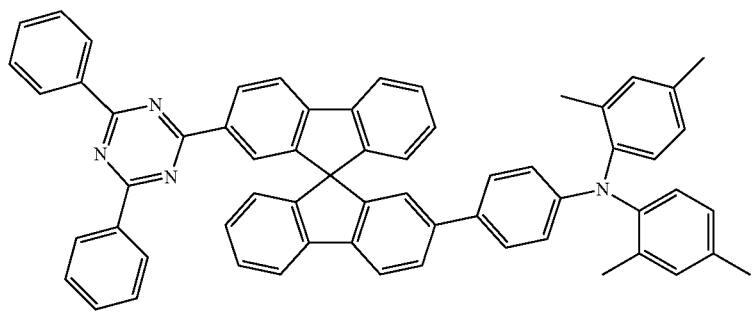
(1-48)
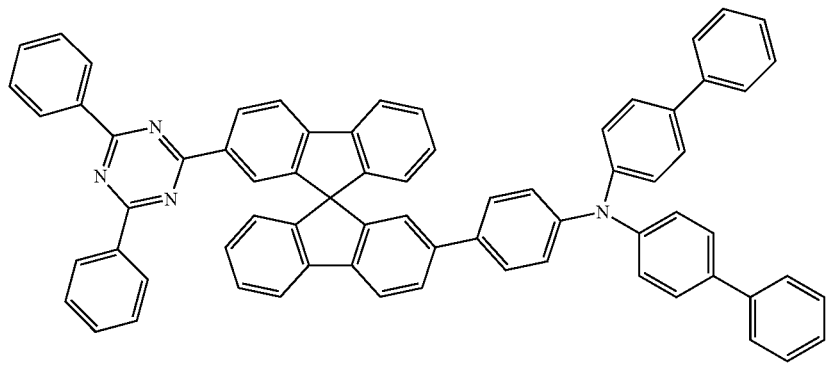
(1-49)
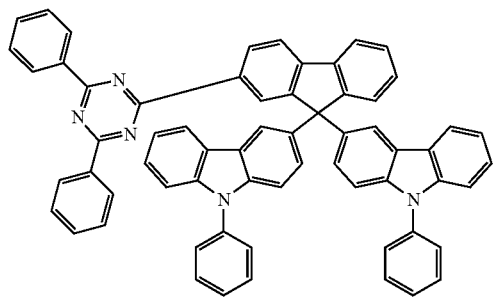
(1-50)
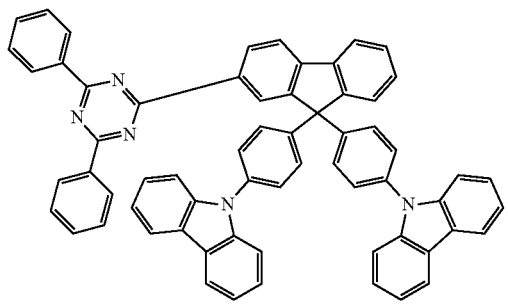

(1-51)
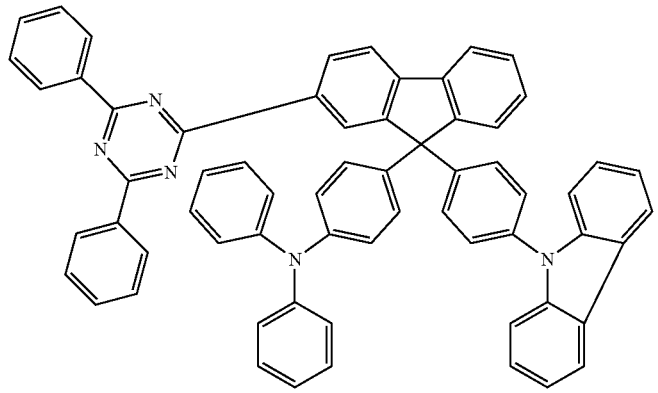
(1-52)
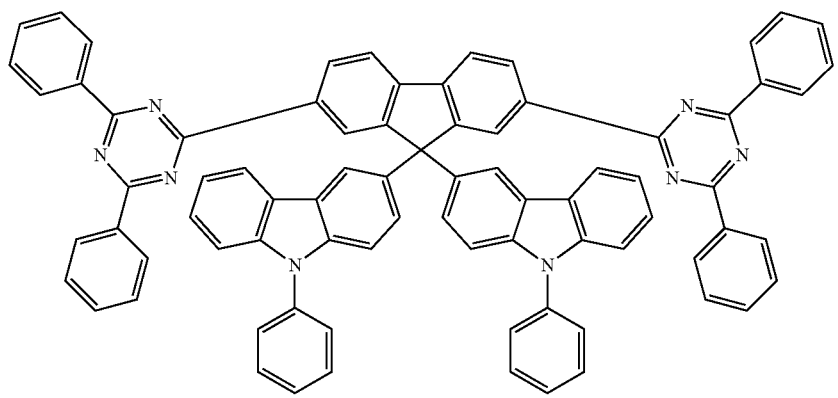
(1-53)
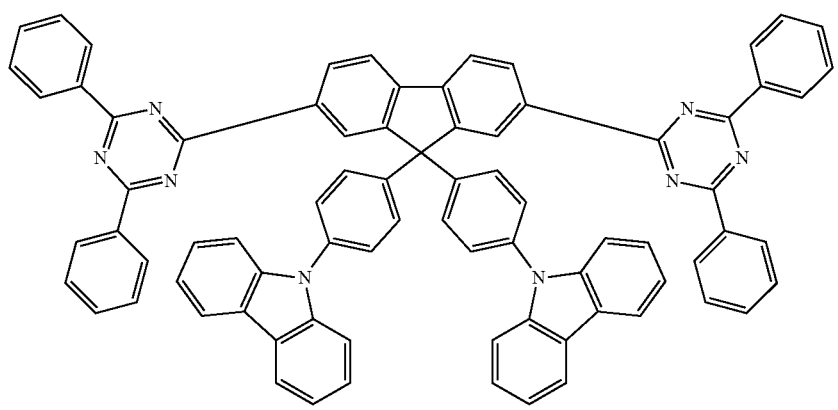
(1-54)
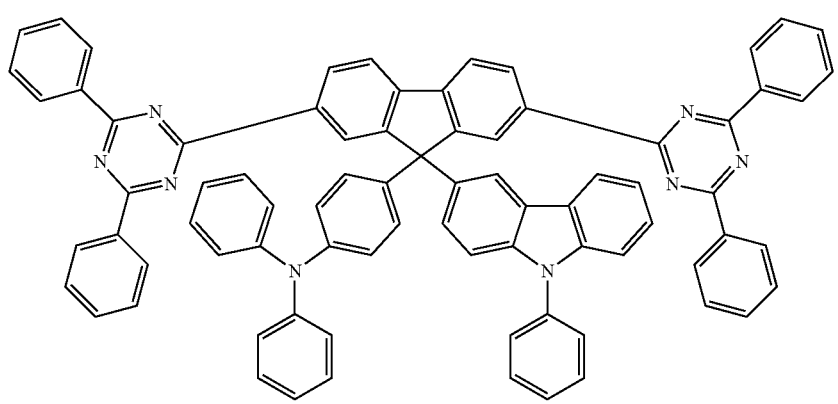

-continued
(1-55)
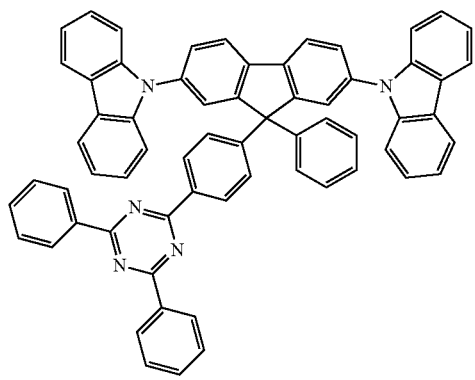
(1-56)
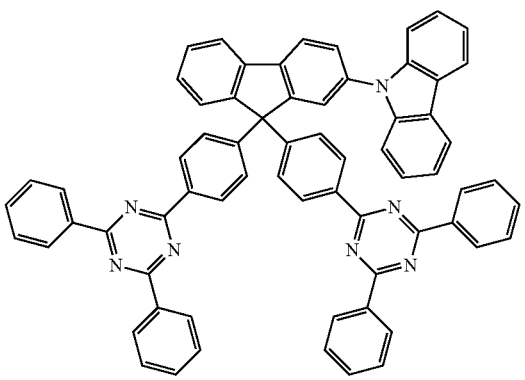
(1-57)
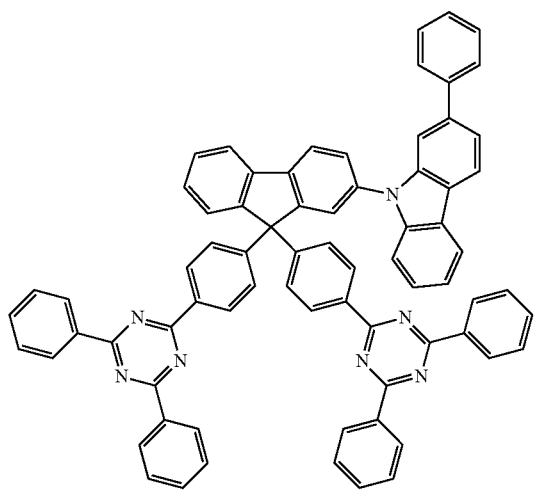
(1-58)
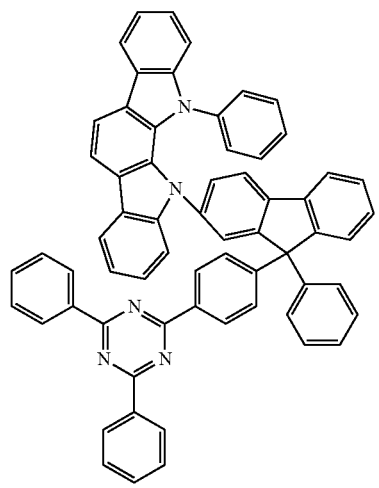
(1-59)
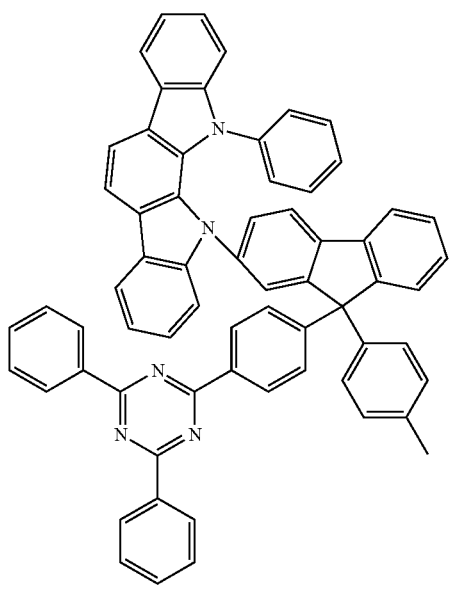

(1-60)
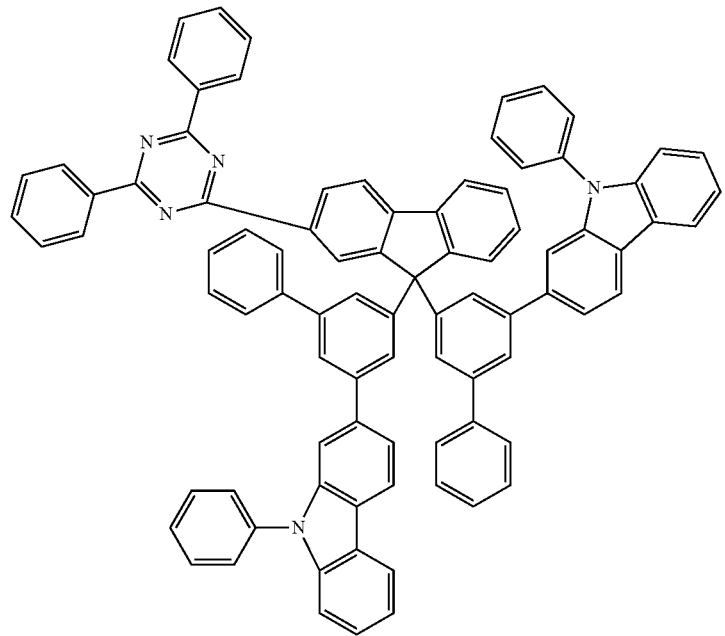
(1-61)
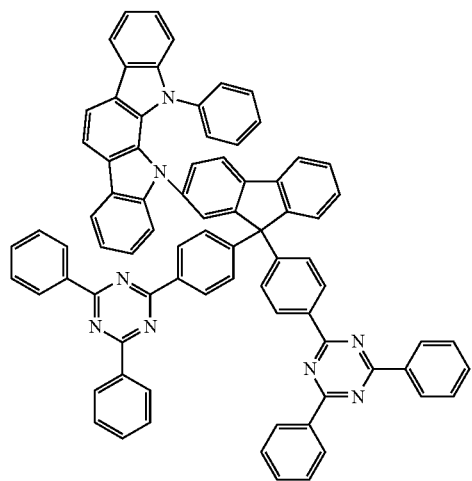
(1-62)
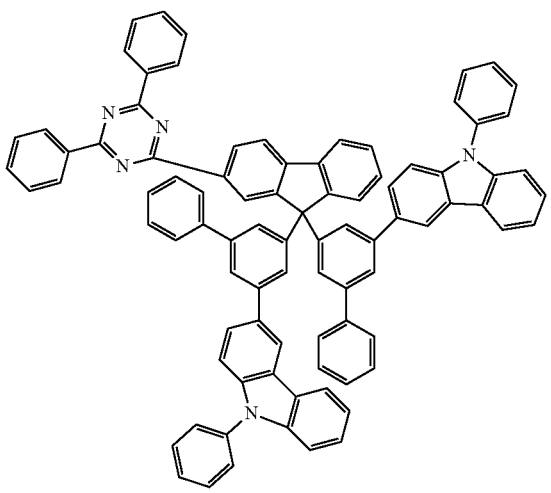

(1-63)
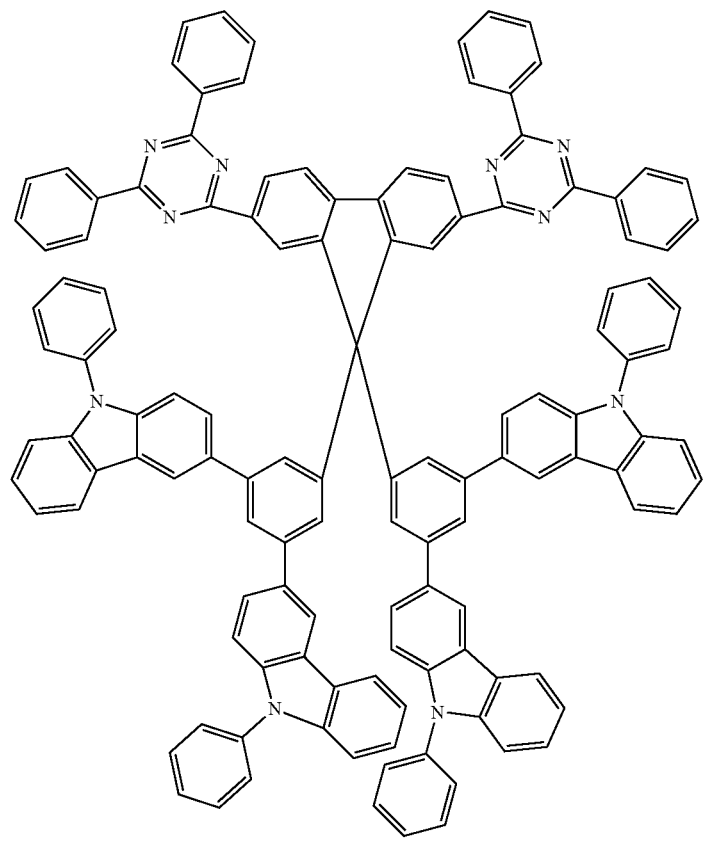
(1-64)
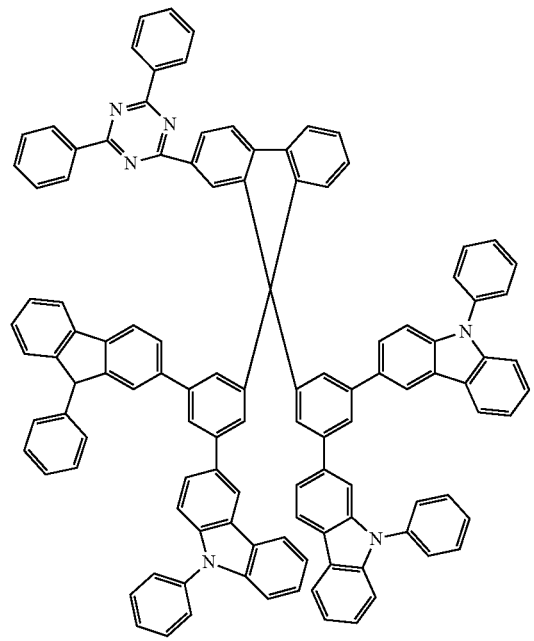
(1-65)
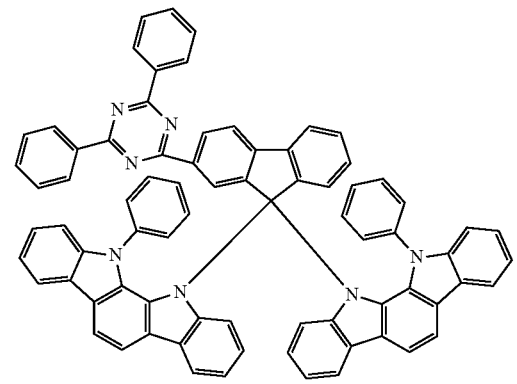

-continued
(1-66)
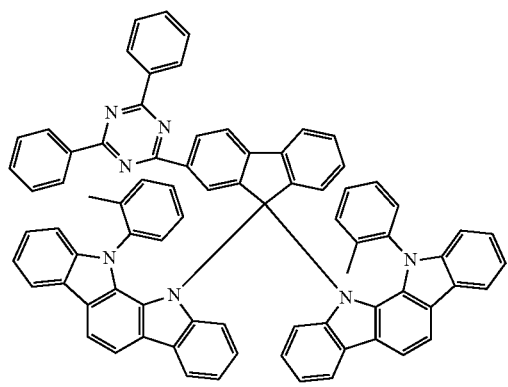
(1-67)
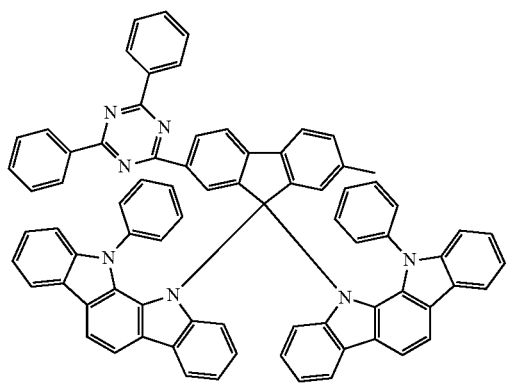
(1-68)
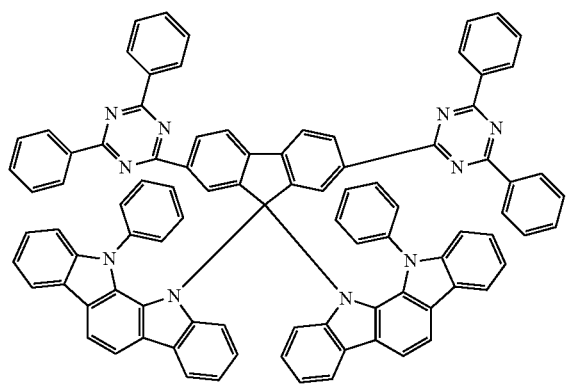
(1-69)
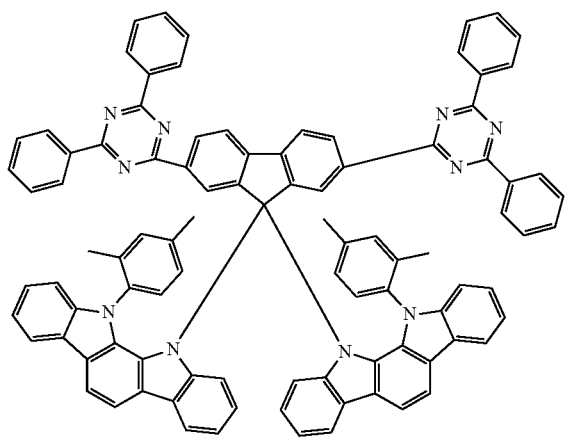
(1-70)
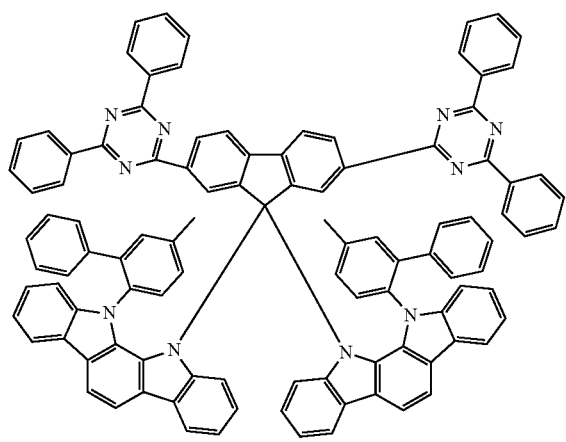
(1-71)
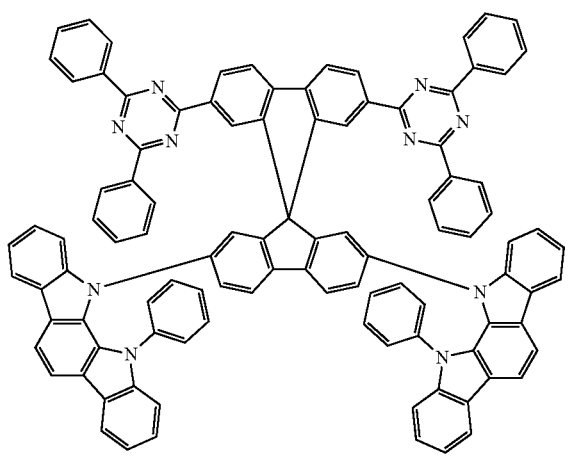

-continued
(1-72)
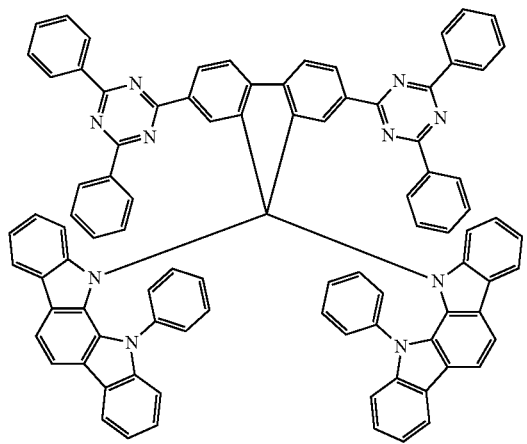
(1-73)
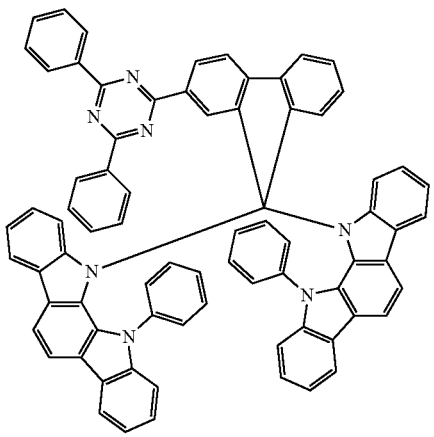
(1-74)
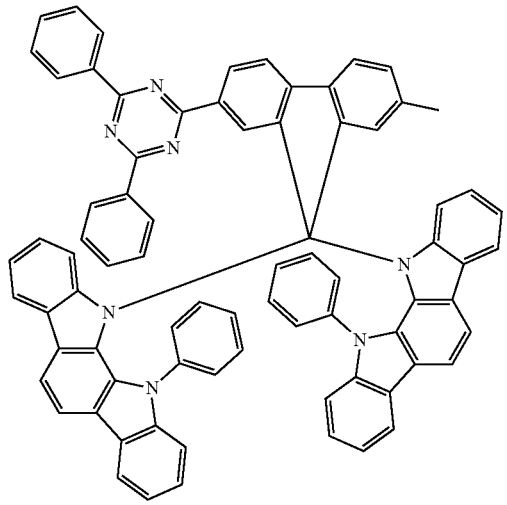
(1-75)
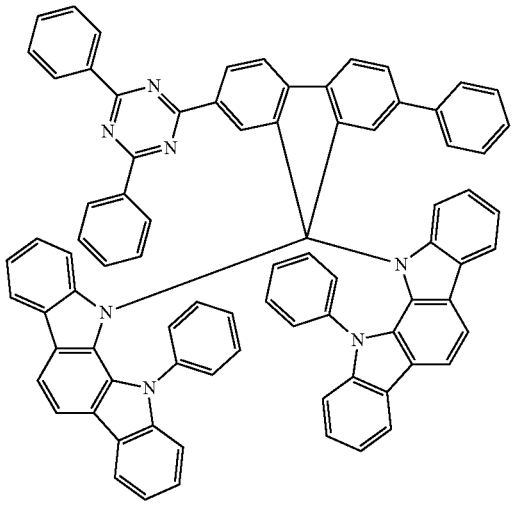
(1-76)
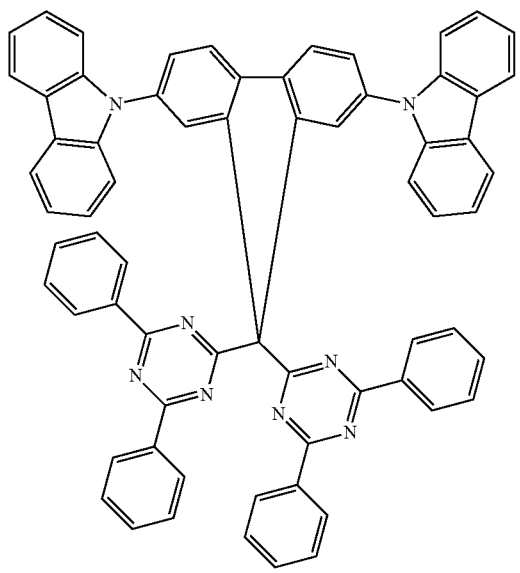

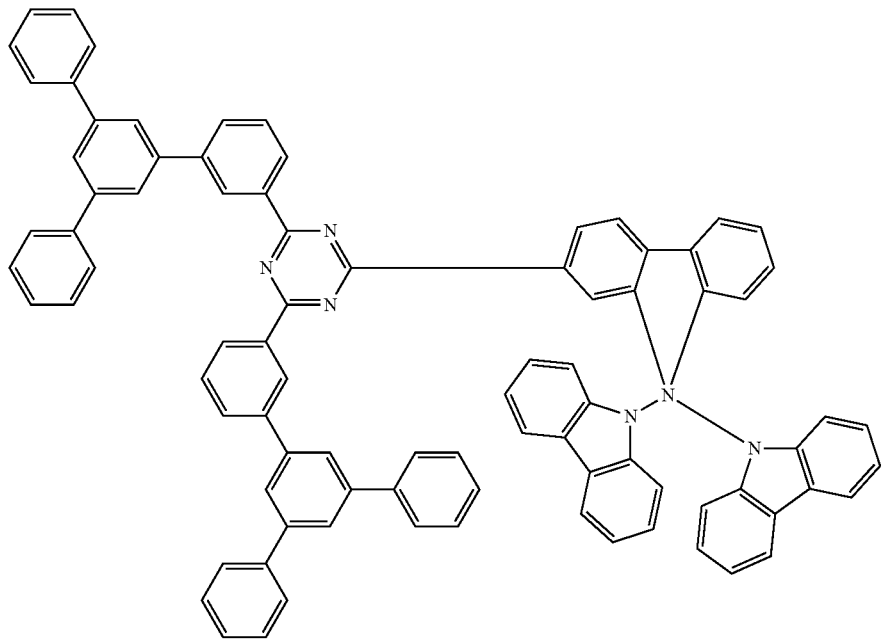
(1-77)
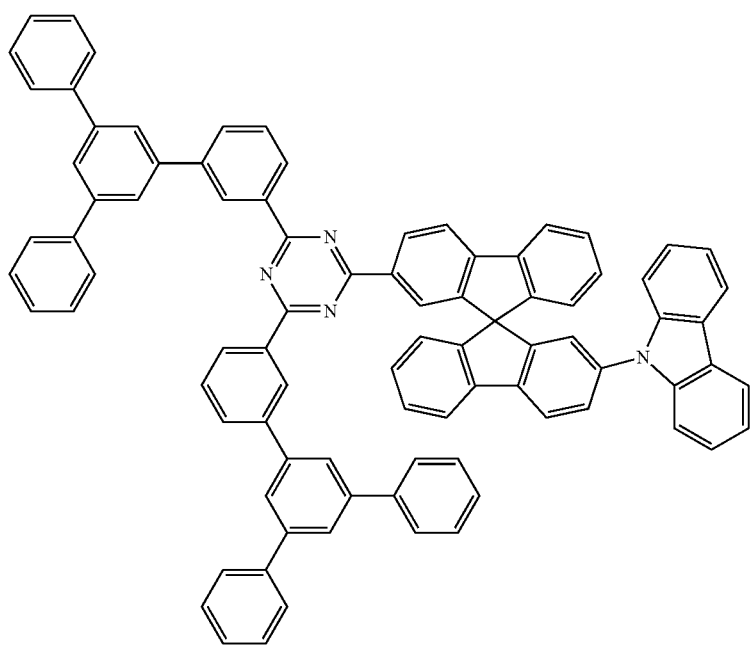
(1-78)
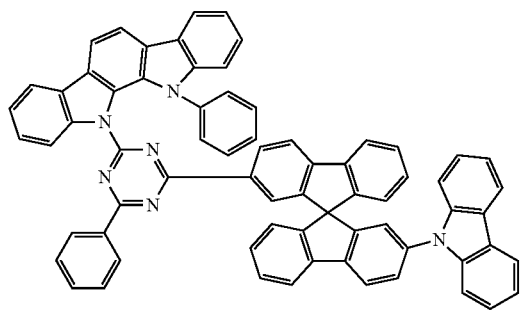
(1-79)
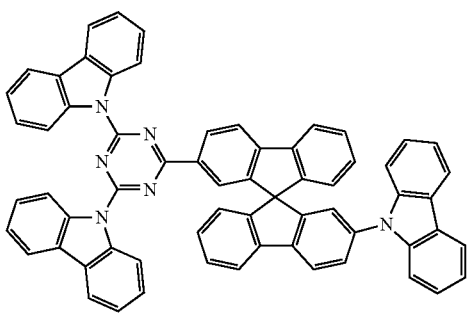
(1-80)

-continued (1-81)

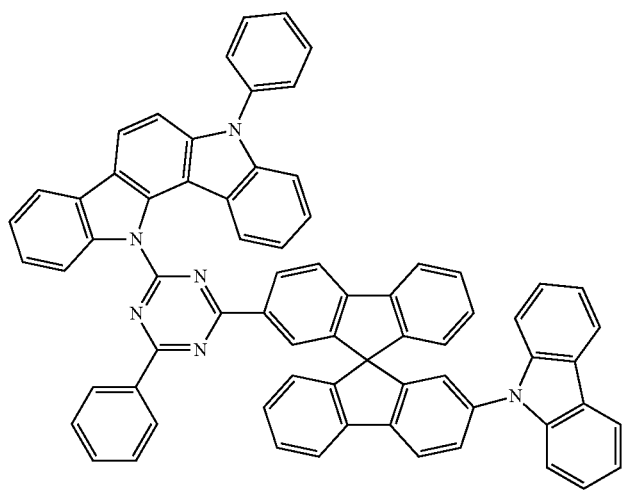

The compounds of the formula (1), (2), (3a) or (3b) can be synthesised, for example, by the processes described in U.S. Pat. Nos. 6,229,012, 6,225,467 and WO 05/053055. In general, metal-catalysed coupling reactions are suitable for the synthesis of the compounds, in particular the Suzuki coupling, as depicted in Scheme 1 below with reference to the example of triazine. Thus, a fluorene or spirobifluorene, each of which is substituted by a boronic acid or boronic acid derivative, can be coupled with palladium catalysis to the group Ar, which is substituted by one reactive leaving group for compounds of the formulae (1), (3a) and (3b) and by two reactive leaving groups for compounds of the formula (2). Suitable reactive leaving groups are, for example, halogens, in particular chlorine, bromine and iodine, triflate and tosylate.

Scheme 1:

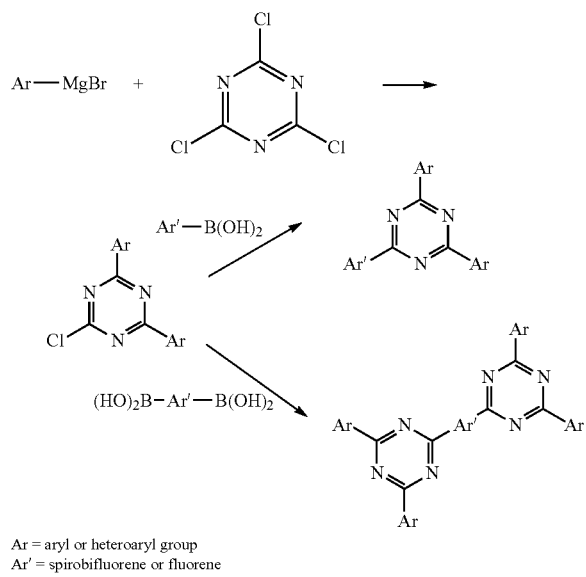

Ar = aryl or heteroaryl group
Ar′ = spirobifluorene or fluorene

As described above, the compounds of the formulae (1), (2), (3a) and (3b) are suitable for use in an electronic device, in particular as matrix materials for phosphorescent emitters. Use as electron-transport material is also possible.

The invention therefore relates to an electronic device, in particular selected from the group consisting of organic electroluminescent devices (OLEDs, PLEDs), organic integrated circuits (O—ICs), organic field-effect transistors (O-FETs), organic thin-film transistors (O-TFTs), organic light-emitting transistors (O-LETs), organic solar cells (O—SCs), organic optical detectors, organic photoreceptors, organic field-quench devices (O-FQDs), light-emitting electrochemical cells (LECs) or organic laser diodes (O-lasers), comprising at least one compound of the above-mentioned formula (1), (2) or (3) in at least one layer.

The invention furthermore also relates to an organic electroluminescent device which comprises the above-mentioned compounds. The compounds according to the invention are particularly preferably a constituent of an emission layer. The organic electroluminescent device preferably comprises the compounds according to the invention as matrix material for phosphorescent emitters. In a further embodiment of the invention, the compounds according to the invention are preferably employed as electron-transport material. In a further embodiment of the invention, the compounds according to the invention are preferably employed both as electron-transport material and also as matrix in one device.

An organic electroluminescent device is taken to mean a device which comprises an anode, a cathode and at least one emitting layer which is arranged between the anode and the cathode, where at least one layer between the anode and the cathode comprises at least one organic or organometallic compound. At least one layer here comprises at least one compound of the above-mentioned formula (1), (2), (3a) or (3b). An organic electroluminescent device need not necessarily comprise only layers built up from organic or organometallic materials. Thus, it is also possible for one or more layers to comprise inorganic materials or to be built up entirely from inorganic materials.

A fluorescent compound in the sense of this invention is a compound which exhibits luminescence from an excited singlet state at room temperature. For the purposes of this invention, in particular, all luminescent compounds which contain no heavy atoms, i.e. no atoms having an atomic number greater than 36, are to be regarded as fluorescent compounds.

A phosphorescent compound in the sense of this invention is a compound which exhibits luminescence from an excited state having relatively high spin multiplicity, i.e. a spin state >1, in particular from an excited triplet state, at room temperature. For the purposes of this invention, in particular, all luminescent transition-metal compounds, in particular all luminescent iridium and platinum compounds, are to be regarded as phosphorescent compounds.

Suitable phosphorescent compounds (emitters) are, in particular, compounds which emit light, preferably in the visible region, on suitable excitation and in addition contain at least one atom having an atomic number greater than 20, preferably greater than 38 and less than 84, particularly preferably greater than 56 and less than 80. The phosphorescent emitters used are preferably compounds which contain copper, molybdenum, tungsten, rhenium, ruthenium, osmium, rhodium, iridium, palladium, platinum, silver, gold or europium, in particular compounds which contain iridium or platinum.

Particularly preferred organic electroluminescent devices comprise, as phosphorescent emitter, at least one compound of the formulae (64) to (67),

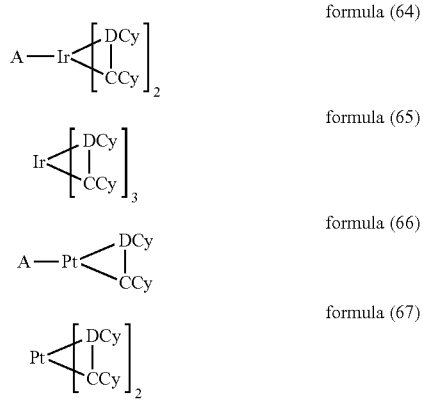

where $R^1$ has the same meaning as described above, and the following applies to the other symbols used:

DCy is, identically or differently on each occurrence, a cyclic group which contains at least one donor atom, preferably nitrogen, carbon in the form of a carbene or phosphorus, via which the cyclic group is bonded to the metal, and which may in turn carry one or more substituents $R^1$; the groups DCy and CCy are connected to one another via a covalent bond;

CCy is, identically or differently on each occurrence, a cyclic group which contains a carbon atom via which the cyclic group is bonded to the metal and which may in turn carry one or more substituents $R^1$;

A is, identically or differently on each occurrence, a monoanionic, bidentate-chelating ligand, preferably a diketonate ligand.

A bridge may also be present between the groups DCy and CCy through the formation of ring systems between a plurality of radicals $R^1$.

Examples of the emitters described above are revealed by the applications WO 00/70655, WO 01/41512, WO 02/02714, WO 02/15645, EP 1191613, EP 1191612, EP 1191614 and WO 05/033244. In general, all phosphorescent complexes, as are used in accordance with the prior art for phosphorescent OLEDs and as are known to the person skilled in the art in the area of organic electroluminescence, are suitable, and the person skilled in the art will be able to use further phosphorescent complexes without an inventive step.

The organic luminescent device according to the invention preferably comprises a cathode, an anode and one or more emitting layers, where at least one emitting layer preferably comprises a compound as defined above. Apart from the cathode, anode and one or more emitting layers, the organic electroluminescent device may also comprise further layers. These are selected, for example, from in each case one or more hole-injection layers, hole-transport layers, hole-blocking layers, electron-transport layers, electron-injection layers, electron-blocking layers, exciton-blocking layers, charge-generation layers and/or organic or inorganic p/n junctions. In addition, interlayers which control the charge balance in the device may be present. Furthermore, the layers, in particular the charge-transport layers, may also be doped. Doping of the layers may be advantageous for improved charge transport. However, it should be pointed out that each of these layers does not necessarily have to be present, and the choice of the layers is always dependent on the compounds used.

In a further preferred embodiment of the invention, the organic electro-luminescent device comprises a plurality of emitting layers, where at least one emitting layer comprises at least one compound of the formula (1), (2), (3a) or (3b) and at least one fluorescent and/or phosphorescent emitter. Alternatively, another layer may also comprise the compound of the formula (1), (2), (3a) or (3b). These emission layers particularly preferably have in total a plurality of emission maxima between 380 nm and 750 nm, resulting overall in white emission, i.e. various emitting compounds which are able to fluoresce or phosphoresce and which emit blue and yellow, orange or red light are used in the emitting layers. Particular preference is given to three-layer systems, i.e. systems having three emitting layers, where at least one of these layers comprises at least one compound of the formula (1), (2), (3a) or (3b) and at least one phosphorescent emitter and where the three layers exhibit blue, green and orange or red emission (for the basic structure see, for example, WO 05/011013). The use of more than three emitting layers may also be preferred. For white emission, emitters which have broad-band emission bands and thus exhibit white emission are likewise suitable.

The emitting layer which comprises the mixture of the compound of the formula (1), (2), (3a) or (3b) and the phosphorescent emitter preferably comprises between 99 and 50% by vol., preferably between 98 and 50% by vol., particularly preferably between 97 and 60% by vol., in particular between 95 and 85% by vol., of the compound of the formula (1), (2), (3a) or (3b), based on the entire mixture comprising emitter and matrix material. Correspondingly, the mixture comprises between 1 and 50% by vol., preferably between 2 and 50% by vol., particularly preferably between 3 and 40% by vol., in particular between 5 and 15% by vol., of the phosphorescent emitter, based on the entire mixture comprising emitter and matrix material.

Preference is furthermore also given to the use of a plurality of matrix materials as a mixture, where one matrix material is selected from compounds of the formulae (1), (2), (3a) and (3b). The compounds of the formulae (1), (2), (3a) and (3b) have predominantly electron-transporting properties due to the electron-deficient nitrogen heterocycles Ar. If a mixture of two or more matrix materials is used, a further component of the mixture is therefore preferably a hole-transporting compound.

Preferred hole-transporting matrix materials are triarylamines, carbazole derivatives, for example CBP (N,N-bis-carbazolylbiphenyl), m-CBP or the carbazole derivatives disclosed in WO 05/039246, US 2005/0069729, JP 2004/

288381, EP 1205527 or WO 08/086851, azacarbazoles, for example in accordance with EP 1617710, EP 1617711, EP 1731584, JP 2005/347160, indolocarbazole derivatives, for example in accordance with WO 07/063754 or WO 08/056746, indenocarbazole derivatives, for example in accordance with the unpublished applications DE 102009023155.2 and DE 102009031021.5, bipolar matrix materials, for example in accordance with WO 07/137725, 9,9-diarylfluorene derivatives, for example in accordance with WO 09/124627, and diazasilole derivatives, for example in accordance with WO 10/054729. The mixture of the matrix materials may also comprise more than two matrix materials. It is furthermore also possible to use the matrix material of the formula (1), (2), (3a) or (3b) as a mixture with a further electron-transporting matrix material. Preferred further electron-transporting matrix materials are ketones, for example in accordance with WO 04/093207 or WO 10/006680, phosphine oxides, sulfoxides and sulfones, for example in accordance with WO 05/003253, oligophenylenes, bipolar matrix materials, for example in accordance with WO 07/137725, silanes, for example in accordance with WO 05/111172, 9,9-diarylfluorene derivatives (for example in accordance with WO 09/124627), azaboroles or boronic esters (for example in accordance with WO 06/117052), diazaphosphole derivatives, for example in accordance with WO 2010/054730, triazine derivatives, for example in accordance with WO 10/015306, WO 07/063754 or WO 08/056746, or zinc complexes, for example in accordance with EP 652273 or WO 09/062578.

It may likewise be preferred for the mixture of the emitting layer to comprise not only one, but instead two or more, phosphorescent emitters.

It has furthermore proven particularly advantageous for the organic electroluminescent device to comprise an electron-transport layer which comprises a triaryl-substituted triazine derivative, preferably compounds of the formula (1), (2), (3a) or (3b) or preferred embodiments thereof, which is doped with an organic alkali-metal compound, or a further layer which comprises an organic alkali-metal compound has been introduced between the electron-transport layer comprising the triaryltriazine and the cathode.

In an embodiment of the invention, the triazine derivative is employed in combination with an organic alkali-metal compound in the electron-transport layer of an organic electroluminescent device. "In combination with an organic alkali-metal compound" here means that the triazine derivative and the alkali-metal compound are either in the form of a mixture in one layer or are present separately in two successive layers. In a preferred embodiment of the invention, the triazine derivative and the organic alkali-metal compound are in the form of a mixture in one layer.

An organic alkali-metal compound in the sense of this invention is intended to be taken to mean a compound which contains at least one alkali metal, i.e. lithium, sodium, potassium, rubidium or caesium, and which furthermore contains at least one organic ligand.

Suitable organic alkali-metal compounds are, for example, the compounds disclosed in WO 07/050301, WO 07/050334 and EP 1144543.

Preferred organic alkali-metal compounds are the compounds of the following formula (62):

formula (62)

where $R^1$ has the same meaning as described above, the curved line represents two or three atoms and bonds which are necessary to make up a 5- or 6-membered ring with M, where these atoms may also be substituted by one or more radicals $R^1$, and M represents an alkali metal selected from lithium, sodium, potassium, rubidium or caesium.

Further preferred organic alkali-metal compounds are the compounds of the following formula (63):

formula (63)

where the symbols used have the same meaning as described above.

The alkali metal is preferably selected from lithium, sodium and potassium, particularly preferably lithium and sodium, very particularly preferably lithium.

Examples of suitable organic alkali-metal compounds are the compounds shown in the following table.

55
-continued
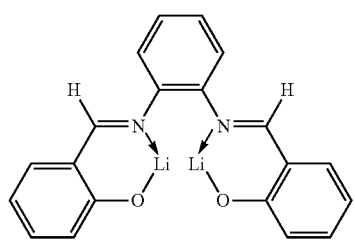
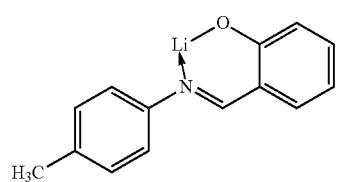
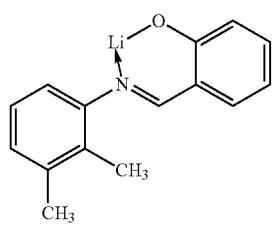
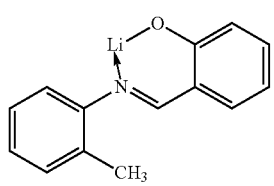
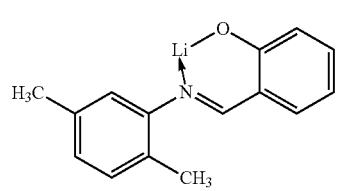
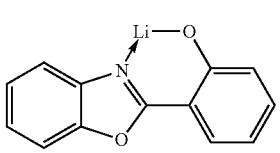
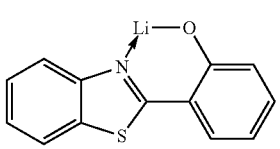
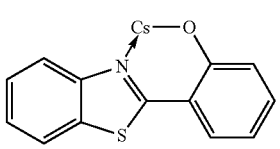
56
-continued
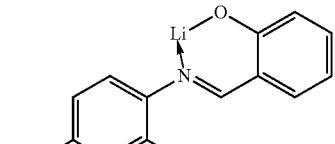
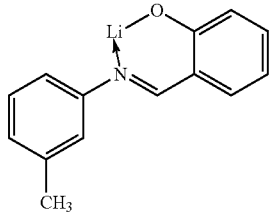
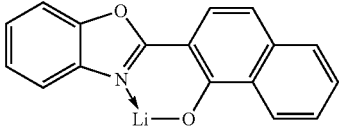
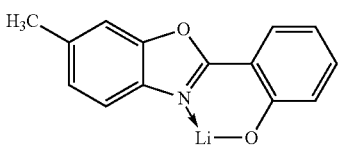
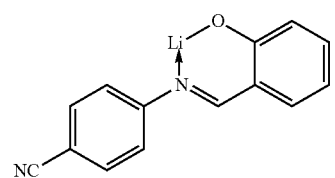
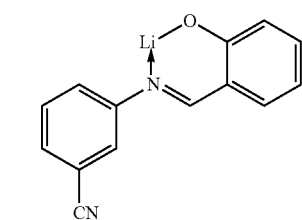
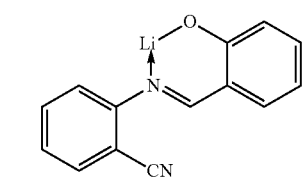
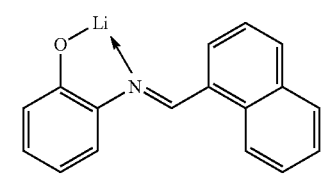
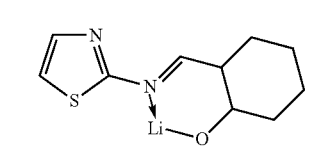

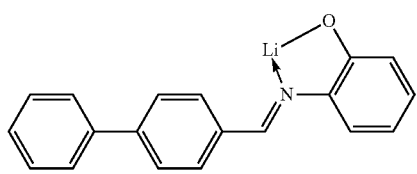
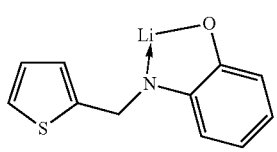
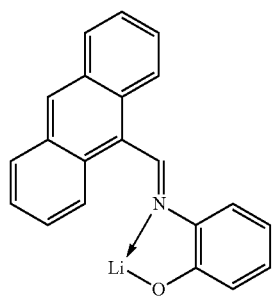
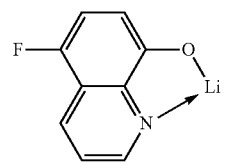
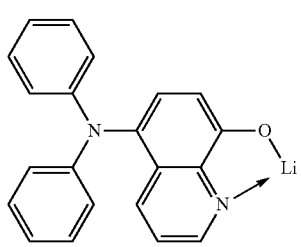
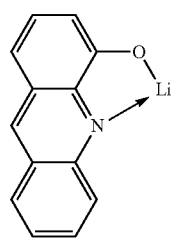
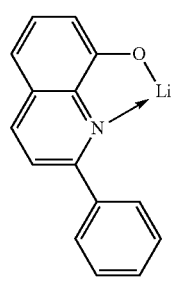
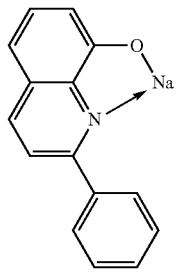
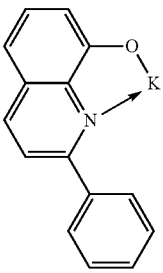
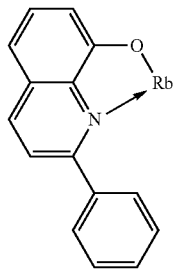
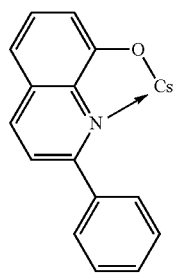
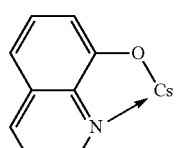
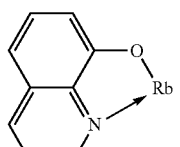
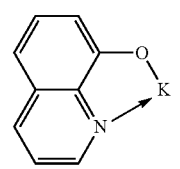

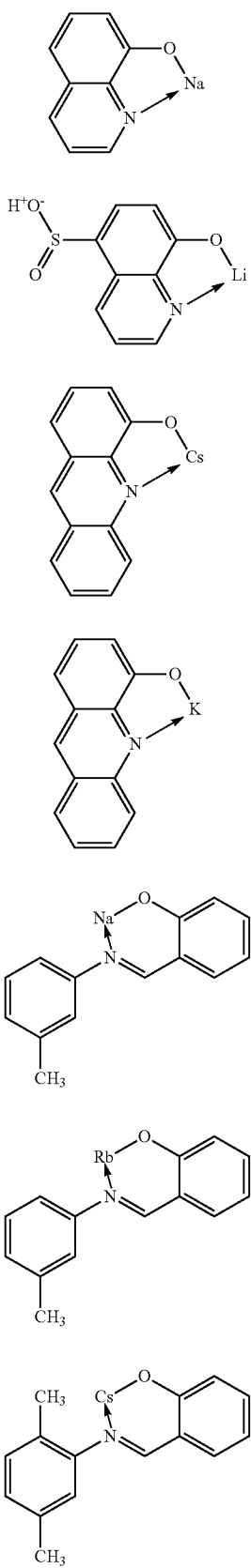

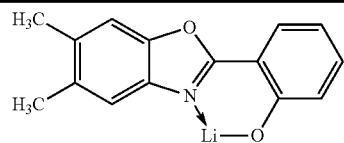

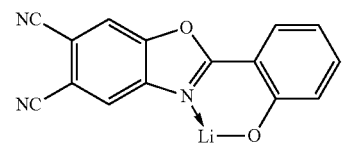

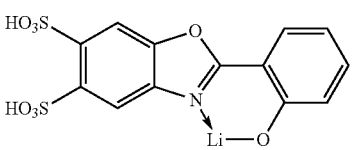

If the triazine compound and the organic alkali-metal compound are in the form of a mixture, the ratio of the triazine compound to the organic alkali-metal compound is preferably 20:80 to 80:20, particularly preferably 30:70 to 70:30, very particularly preferably 30:70 to 50:50, in particular 30:70 to 45:55. The organic alkali-metal compound is thus particularly preferably present in a higher proportion than the triazine compound.

If the triazine compound and the organic alkali-metal compound are in the form of a mixture, the layer thickness of this electron-transport layer is preferably between 3 and 150 nm, particularly preferably between 5 and 100 nm, very particularly preferably between 10 and 60 nm, in particular between 15 and 40 nm.

If the triazine compound and the organic alkali-metal compound are present in two successive layers, the layer thickness of the layer which comprises the triazine compound is preferably between 3 and 150 nm, particularly preferably between 5 and 100 nm, very particularly preferably between 10 and 60 nm, in particular between 15 and 40 nm. The layer thickness of the layer which comprises the organic alkali-metal compound and which is arranged between the triazine layer and the cathode is preferably between 0.5 and 20 nm, particularly preferably between 1 and 10 nm, very particularly preferably between 1 and 5 nm, in particular between 1.5 and 3 nm.

The emitting layer here can be a fluorescent or phosphorescent layer. In general, all known emitting materials and layers are suitable in combination with the electron-transport layer according to the invention, and the person skilled in the art will be able to combine any desired emitting layers with the electron-transport layer according to the invention without an inventive step. Combination with an emitting layer which comprises at least one compound of the formula (1), (2), (3a) or (3b), as defined above, is likewise preferred.

The electron-transport layers according to the invention can be employed with any desired cathode materials, as used in accordance with the prior art. Examples of particularly suitable cathode materials are generally metals having a low work function, followed by a layer of aluminium or a layer of silver. Examples thereof are caesium, barium, calcium, ytterbium and samarium, in each case followed by a layer of aluminium or silver. An alloy comprising magnesium and silver is furthermore suitable.

It is furthermore possible to introduce an electron-injection layer between the electron-transport layer according to the invention and the cathode. Suitable materials for the electron-injection layer are, for example, LiF, lithium quinolinate, CsF, $Cs_2CO_3$, $Li_2O$, $LiBO_2$, $K_2SiO_3$, $Cs_2O$ or $Al_2O_3$.

Preference is furthermore given to an organic electroluminescent device, characterised in that one or more layers are applied by means of a sublimation method, in which the materials are applied by vapour deposition in vacuum sublimation units at an initial pressure of less than $10^{-5}$ mbar, preferably less than $10^{-6}$ mbar. However, it should be noted that the pressure may also be even lower, for example less than $10^{-7}$ mbar.

Preference is likewise given to an organic electroluminescent device, characterised in that one or more layers are applied by means of the OVPD (organic vapour phase deposition) method or with the aid of carrier-gas sublimation, in which the materials are applied at a pressure of between $10^{-5}$ mbar and 1 bar. A special case of this method is the OVJP (organic vapour jet printing) method, in which the materials are applied directly through a nozzle and are thus structured (for example M. S. Arnold et al., *Appl. Phys. Lett.* 2008, 92, 053301).

Preference is furthermore given to an organic electroluminescent device, characterised in that one or more layers are produced from solution, such as, for example, by spin coating, or by means of any desired printing process, such as, for example, screen printing, flexographic printing, nozzle printing or offset printing, but particularly preferably LITI (light induced thermal imaging, thermal transfer printing) or ink-jet printing. Soluble compounds are necessary for this purpose. High solubility can be achieved through suitable substitution of the compounds. It is not only solutions of individual materials that can be applied here, but also solutions which comprise a plurality of compounds, for example matrix materials and dopants.

The organic electroluminescent device can also be produced as a hybrid system by applying one or more layers from solution and applying one or more other layers by vapour deposition. Thus, for example, it is possible to apply an emitting layer comprising a compound of the formula (1), (2), (3a) or (3b) and a phosphorescent dopant from solution and to apply a hole-blocking layer and/or an electron-transport layer on top by vacuum vapour deposition. The emitting layer comprising a compound of the formula (1), (2), (3a) or (3b) and a phosphorescent dopant can likewise be applied by vacuum vapour deposition and one or more other layers can be applied from solution.

These methods are generally known to the person skilled in the art and can be applied by him without problems to organic electroluminescent devices comprising compounds of the formula (1), (2), (3a) or (3b) or the preferred embodiments indicated above.

The present invention furthermore relates to mixtures comprising at least one phosphorescent emitter and at least one compound of the formula (1), (2), (3a) or (3b).

The invention furthermore relates to solutions or formulations comprising a mixture of at least one phosphorescent emitter and at least one compound of the formula (1), (2), (3a) or (3b) and at least one preferably organic solvent.

The invention furthermore relates to solutions or formulations comprising a mixture of at least one compound of the formula (1), (2), (3a) or (3b) and at least one preferably organic solvent.

The present invention again furthermore relates to the use of compounds of the formula (1), (2), (3a) or (3b) as matrix material for phosphorescent emitters in an organic electroluminescent device or as electron-transport material.

The organic electroluminescent devices according to the invention have the following surprising advantages over the prior art:
1. The organic electroluminescent devices according to the invention have very high efficiency.
2. The organic electroluminescent devices according to the invention at the same time have an improved lifetime.
3. The organic electroluminescent devices according to the invention at the same time have a reduced operating voltage.
4. The above-mentioned improved properties of the organic electroluminescent devices are obtained not only with tris-ortho-metallated metal complexes, but, in particular, also with complexes which also contain a ketoketon ate ligand, for example acetyl acetonate.

The invention is described in greater detail by the following examples without wishing to restrict it thereby. The person skilled in the art will be able, without being inventive, to prepare further compounds according to the invention and to use them in electronic devices and to carry out the invention throughout the range claimed.

EXAMPLES

The following syntheses are carried out, unless indicated otherwise, under a protective-gas atmosphere in dried solvents. The starting materials can be purchased from ALDRICH (potassium fluoride (spray-dried), tri-tert-butylphosphine, palladium(II) acetate). 3-Chloro-5,6-diphenyl-1,2,4-triazine can be prepared analogously to EP 577559. 2',7'-Di-tert-butylspiro-9,9'-bifluorene-2,7-bisboronic acid glycol ester can be prepared in accordance with WO 02/077060, and 2-chloro-4,6-diphenyl-1,3,5-triazine can be prepared in accordance with U.S. Pat. No. 5,438,138. Spiro-9,9'-bifluorene-2,7-bis(boronic acid glycol ester) can be prepared analogously to WO 02/077060.

As the starting point, 2,2'-diiodo-9,9'-spirobifluorene, for example, can be prepared analogously to: European Journal of Organic Chemistry 2005, (10), 1991-2001. 2',7'-Dibromo-spiro-9,9'-bifluorene-2-carbonyl chloride can be prepared in accordance with J. Org. Chem. 2006, 71 (2), 456-465.

Synthesis Scheme (1):

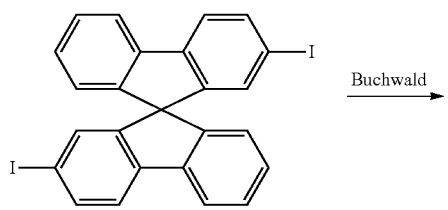

-continued

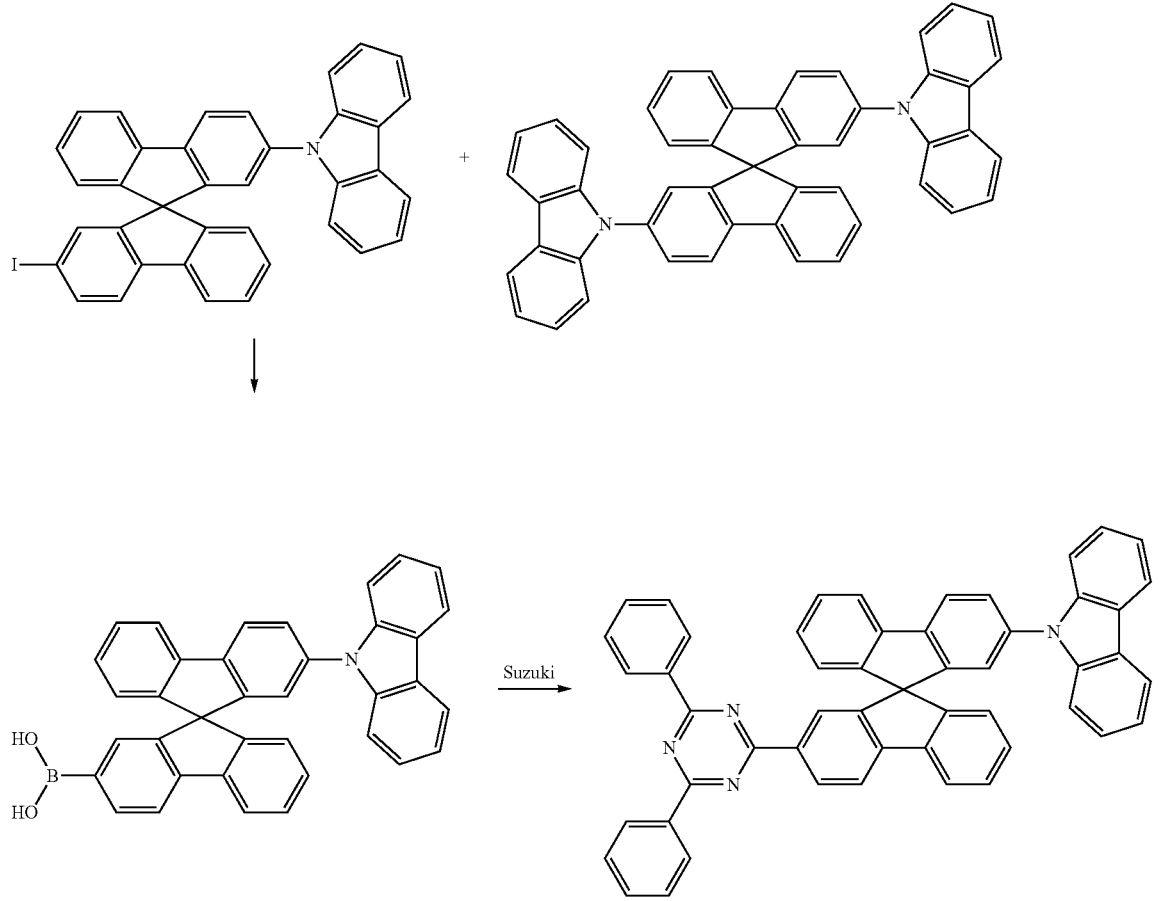

| Example 1 | Example 2 |
|---|---|
| 2-Iodo-7'-9H-carbazole-9,9'-spirobifluorene | 2-Iodo-7'-9H-carbazole-9,9'-spirobifluorene-2-boronic acid glycol ester |

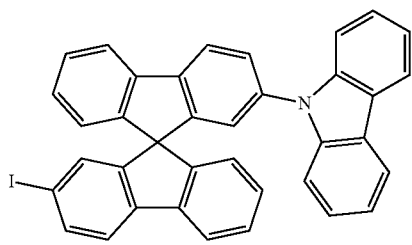 [SMILES: Ic1ccc2c(c1)C1(c3ccccc3-2)c2ccccc2-c2ccc(-n3c4ccccc4c4ccccc43)cc21]

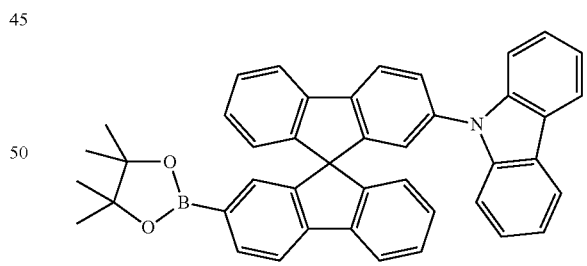

A degassed solution of 23.3 g (140 mmol) of carbazole and 204 g (352 mmol) of 2,2'-diiodo-9,9'-spirobifluorene in 250 ml of xylene is saturated with $N_2$ for 1 h. Then, firstly 3 ml (12.2 mmol) of P($^t$Bu)$_3$, then 0.5 g (2.45 mmol) of palladium acetate are added to the solution, and 81.9 g (956 mmol) of $K_3PO_4$ in the solid state are subsequently added. The reaction mixture is heated under reflux for 18 h. After cooling to room temperature, 1000 ml of water are carefully added. The organic phase is washed with 4×50 ml of $H_2O$, dried over $MgSO_4$, and the solvents are removed in vacuo. The pure product is obtained by recrystallisation. The yield is 47 g (76 mmol), corresponding to 55% of theory.

118 g (190 mmol) of 2-iodo-7'-9H-carbazole-9,9'-spirobifluorene are dissolved in 1500 ml of dry diethyl ether, 420 ml (840 mmol) of a 2 M solution of n-butyllithium in cyclohexane are added dropwise at −70° C., 130 ml of trimethyl borate (1140 mmol) are added dropwise after 1 h, the mixture is warmed to room temperature over the course of 1 h, the solvent is removed, 90 g (76 mmol) of pinacol and 1000 ml of toluene are added, the mixture is heated at the boil for 2 h, the solvent is removed again, and the residue, which is uniform according to $^1$H-NMR, is employed without further purification in the subsequent reaction. The yield is 75 g (120 mmol), corresponding to 64% of theory.

Example 3

2-(4,6-Diphenyl-1,3,5-triazin-2-yl)-7'-9H-carbazole-9,9'-spirobifluorene

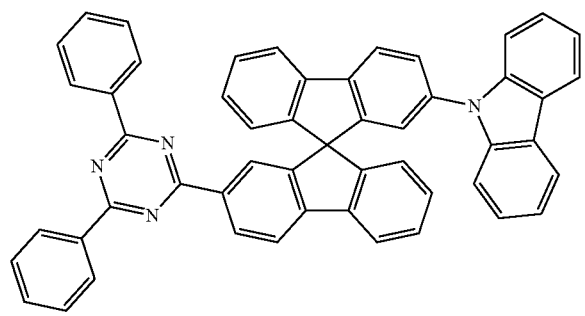 [SMILES: c1ccc(-c2nc(-c3ccccc3)nc(-c3ccc4c(c3)C3(c5ccccc5-4)c4ccccc4-c4ccc(-n5c6ccccc6c6ccccc65)cc43)n2)cc1]

68 g (110.0 mmol) of 2-iodo-7'-9H-carbazole-9,9'-spirobifluoreneboronic acid glycol ester, 29.5 g (110.0 mmol) of 2-chloro-4,6-diphenyl-1,3,5-triazine and 44.6 g (210.0 mmol) of tripotassium phosphate are suspended in 500 ml of toluene, 500 ml of dioxane and 500 ml of water. 913 mg (3.0 mmol) of tri-o-tolylphosphine and then 112 mg (0.5 mmol) of palladium(II) acetate are added to this suspension, and the reaction mixture is heated under reflux for 16 h. After cooling, the organic phase is separated off, filtered through silica gel, washed three times with 200 ml of water and subsequently evaporated to dryness. The residue is recrystallised from toluene and from dichloromethane/isopropanol and finally sublimed in a high vacuum. The purity is 99.9%. The yield is 67 g (92 mmol), corresponding to 85% of theory.

Synthesis Scheme (2):

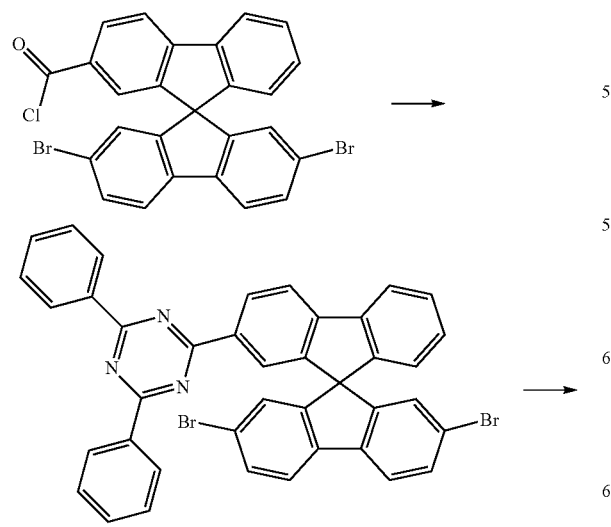

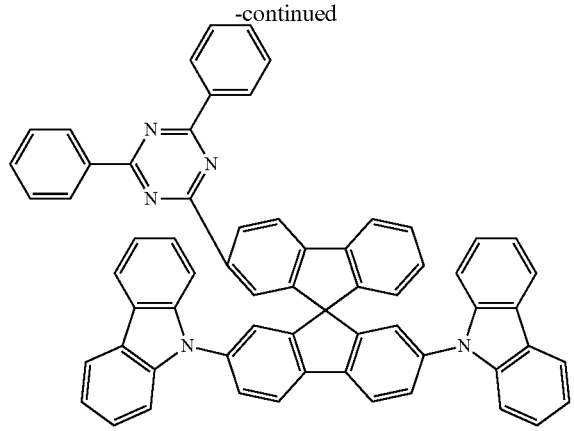

Example 4

2-(4,6-Diphenyl-1,3,5-triazin-2-yl)-2',7'-dibromo-spiro-9,9'-bifluorene

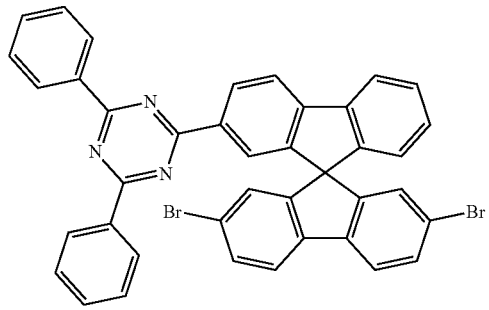 [SMILES: Brc1ccc2c(c1)C1(c3ccccc3-c3ccc(-c4nc(-c5ccccc5)nc(-c5ccccc5)n4)cc31)c1cc(Br)ccc1-2]

47.90 g (89 mmol) of 2',7'-dibromo spiro-9,9'-bifluorene-2-carbonyl chloride, 11.90 g (89 mmol) of aluminium trichloride and 1.9 ml (27 mmol) of thionyl chloride are suspended in 260 ml of dichlorobenzene. 19.3 ml (187 mmol) of benzonitrile are then added slowly. The reaction mixture is stirred at 100° C. for 1 h. 9.55 g (179 mmol) of ammonium chloride are added, and the batch is stirred at 100° C. for 16 h. After cooling to room temperature, the reaction solution is poured into 3.5 l of methanol and stirred for 45 min. The precipitated solid is filtered off and recrystallised from toluene. The yield is 18.8 g (26.7 mmol), corresponding to 29.8% of theory.

Example 5

2-(4,6-Diphenyl-1,3,5-triazin-2-yl)-2', 7'-9H-carbazolespiro-9,9'-bifluorene

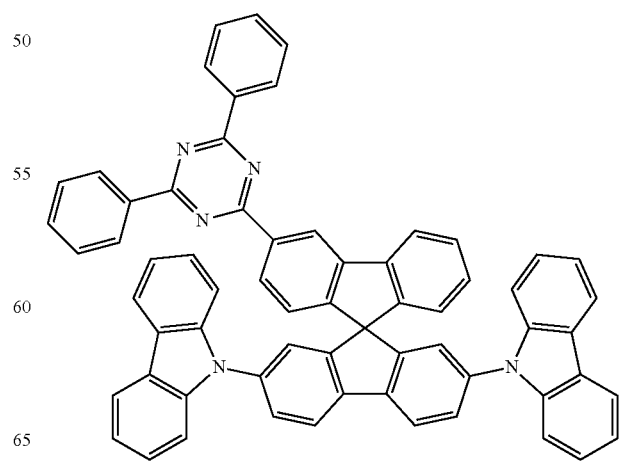

The synthesis is carried out analogously to Example 1, with the 2,2'-diiodo-9,9'-spirobifluorene being replaced by 15.8 g (22.0 mmol) of 2-(4,6-diphenyl-1,3,5-triazin-2-yl)-2',7'-dibromospiro-9,9'-bifluorene. The residue is recrystallised from toluene and from dichloromethane/isopropanol and finally sublimed in a high vacuum. The purity is 99.9%. The yield is 17.6 g (13.7 mmol), corresponding to 62% of theory.

Example 6

Production and Characterisation of Organic Electroluminescent Devices Comprising Triazine Compounds Electroluminescent devices according to the invention can be produced as described, for example, in WO 05/003253. The results for various OLEDs are compared here. The basic structure, the materials used, the degree of doping and the layer thicknesses thereof are identical for better comparability. Examples 7, 8 and 13 describe comparative standards in accordance with the prior art, in which the emission layer consists of a spirobifluorenyltriazine derivative (T) as host material (or matrix material) and various guest materials (dopants) TER for red or TEG for green triplet emission. Furthermore, OLEDs which comprise the spirobifluorenyltriazinylcarbazole derivatives as host material are described. The OLEDs having the following structure are produced analogously to the general process mentioned above:

| | |
|---|---|
| Hole-injection layer (HIL) | 20 nm of 2,2',7,7'-tetrakis(di-para-tolyl-amino)spiro-9,9'-bifluorene |
| Hole-transport layer (HTL) | 20 nm of NPB (N-naphthyl-N-phenyl-4,4'-diaminobiphenyl) |
| Emission layer (EML) | 40 nm of host material: spirobifluorenyl-triazine derivative (T) or compounds according to the invention Dopant: 15% by vol. doping; compounds see below |
| Hole-blocking layer (HBL) | 10 nm of T (optional) |
| electron-transport layer (ETL) | 20 nm of AlQ$_3$ (tris(quinolinato)aluminium (III)) |
| Cathode | 1 nm of LiF, 100 nm of Al on top. |

The structures of TER-1, TER-2, TEG and T are depicted below for clarity.

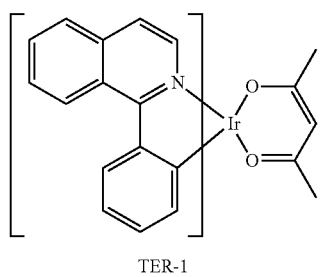

TER-1

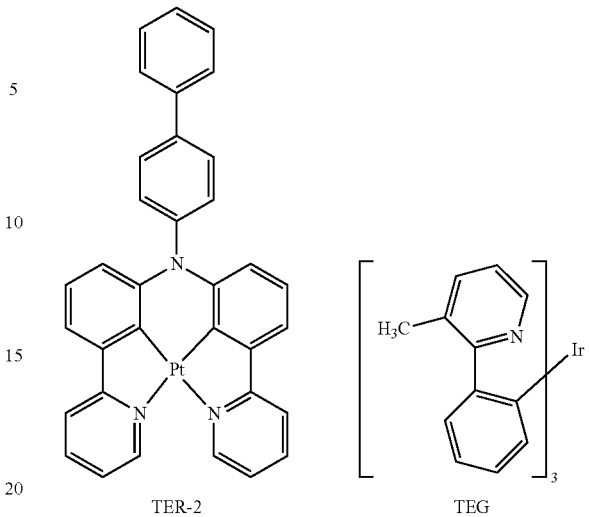

TER-2      TEG

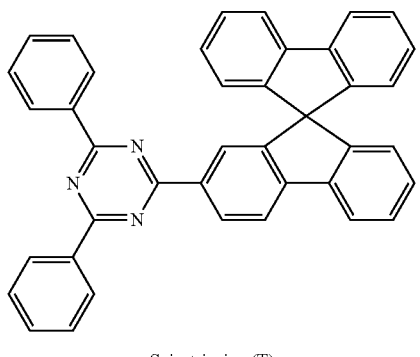

Spirotriazine (T)

The spirotriazinylcarbazoles triazinylcarbazole 1 and triazinylcarbazole 2 used have the structures depicted below.

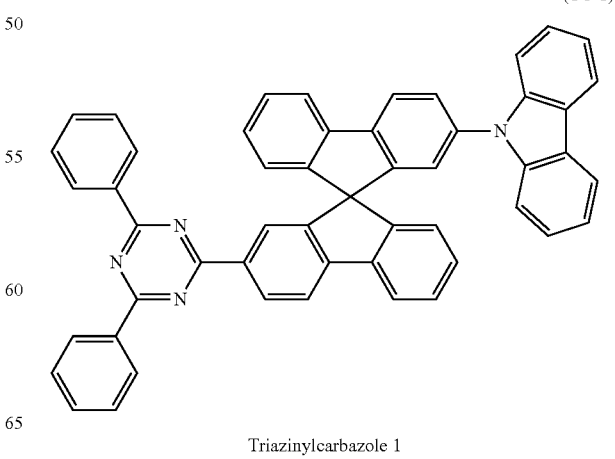

(TC-1)

Triazinylcarbazole 1

-continued

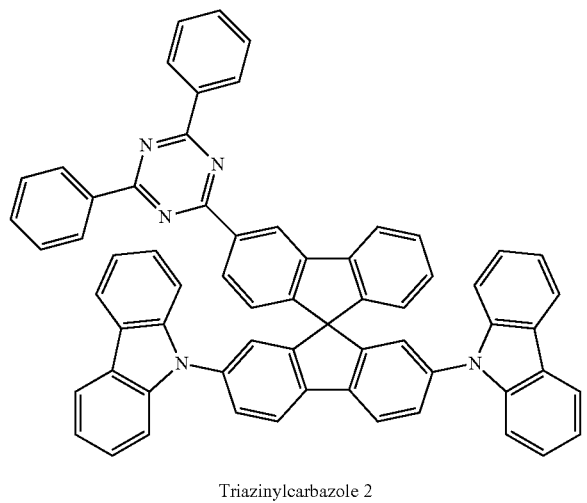

Triazinylcarbazole 2 (TC-2)

These as yet unoptimised OLEDs are characterised by standard methods; for this purpose, the electroluminescence spectra, the efficiency (measured in cd/A) as a function of the luminance, the operating voltage, calculated from current/voltage/luminance characteristic lines (IUL characteristic lines), and the lifetime are determined.

As can be seen from Tables 1 and 2, devices surprisingly exhibit a superior behaviour in the measured efficiencies, voltages and lifetimes compared with the comparative devices comprising the host material T.

TABLE 1

Device results with TC-1 or TC-2 in combination with TER-1 or TER-2 as dopant

| Ex. | EML (with HBL) | Max. eff. [cd/A] at 1000 cd/m² | Voltage [V] at 1000 cd/m² | CIE (x, y) | Lifetime [h], initial luminance 1000 cd/m² |
|---|---|---|---|---|---|
| 7 (comp.) | T: TER-1 | 7.2 | 5.0 | 0.69/0.31 | 14000 |
| 8 (comp.) | T: TER-2 | 9.0 | 6.5 | 0.66/0.33 | 18000 |
| 9 | TC-1: TER-1 | 7.9 | 4.5 | 0.69/0.31 | 19000 |
| 10 | TC-1: TER-2 | 9.2 | 6.3 | 0.66/0.33 | 21000 |
| 11 | TC-2: TER-1 | 8.3 | 4.7 | 0.69/0.31 | 22000 |
| 12 | TC-2: TER-2 | 9.5 | 6.1 | 0.66/0.33 | 28000 |

TABLE 2

Device results with TC-1 in combination with TEG as dopant

| Ex. | EML (with HBL) | Max. eff. [cd/A] at 1000 cd/m² | Voltage [V] at 1000 cd/m² | CIE (x, y) | Lifetime [h], initial luminance 1000 cd/m² |
|---|---|---|---|---|---|
| 13 (comp.) | T: TEG | 35 | 4.7 | 0.36/0.61 | 25000 |
| 14 | TC-1: TEG | 38 | 4.2 | 0.36/0.61 | 32000 |

Analogously to the above-mentioned structure, it can also be shown that the compounds according to the invention are suitable as electron-transport materials. This is shown with reference to the example of a blue-fluorescent device having basically the above structure. The following matrix M and emitter D having a degree of doping of 5% are used for this purpose.

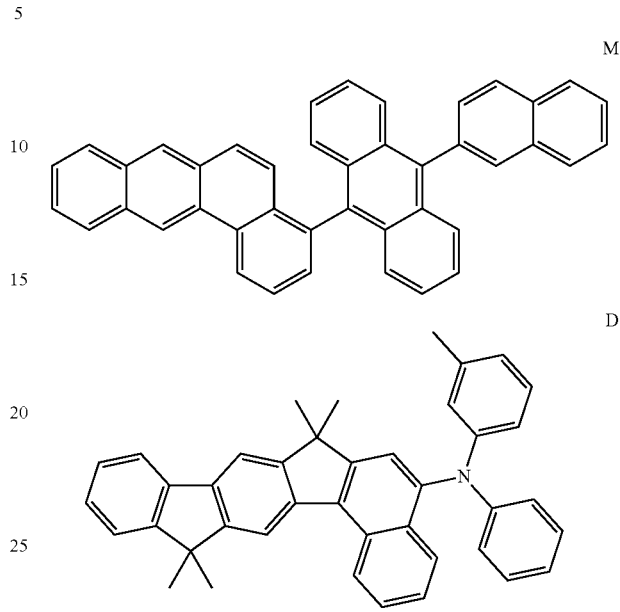

The layer thickness of the emission layer is 30 nm and the layer thickness of the electron-transport layer is 20 nm.

The results are shown in Table 3. An improvement in the efficiency and the requisite voltage is observed. In Comparative Example 15, a lifetime of about 6000 h is obtained at 1000 cd/m². The lifetimes of Examples 16 and 17 according to the invention are comparable.

TABLE 3

Device results with TC-1 or TC-2 as ETM compared with Alq₃ as ETM.

| Ex. | ETL | Max. eff. [cd/A] at 1000 cd/m² | Voltage [V] at 1000 cd/m² | CIE (x, y) |
|---|---|---|---|---|
| 15 (comp.) | Alq$_3$ | 5.1 | 6.4 | 0.14/0.15 |
| 16 | TC-1 | 8.2 | 4.3 | 0.14/0.15 |
| 17 | TC-2 | 8.0 | 4.4 | 0.14/0.15 |

The invention claimed is:

1. A compound of the formula (1), (2), (3a) or (3b),

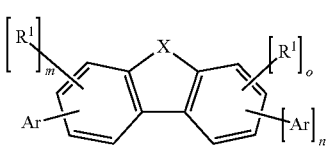

formula (1)

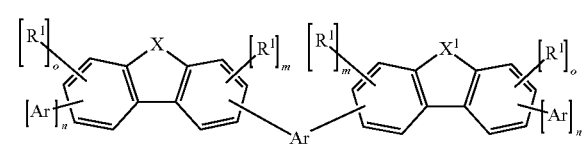

formula (2)

-continued formula (3a)

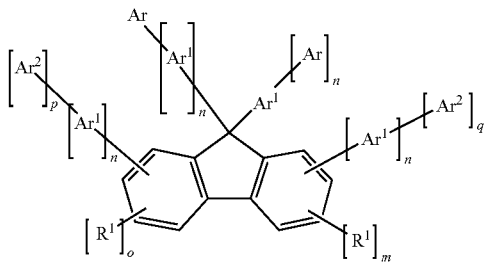

formula (3b)

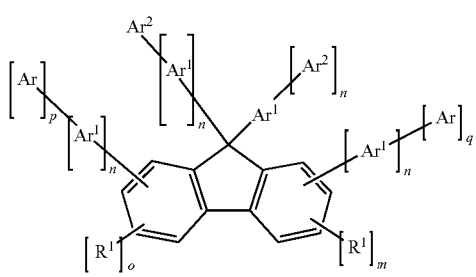

where the following applies to the symbols and indices used:
Ar is on each occurrence, identically or differently, a heteroaryl group selected from the group consisting of triazine, pyrazine, pyrimidine, pyridazine, pyridine, pyrazole, imidazole, oxazole, 1,3,4-oxadiazole, benzimidazole or thiazole, each of which is optionally substituted by one or more groups $R^1$;
X is a group of the formula (4), where the dashed bond in each case indicates the bond to the two benzene rings:

formula (4)

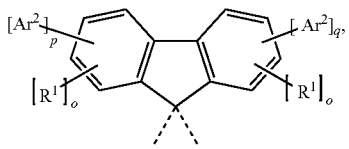

or X is on each occurrence, identically or differently, a divalent bridge selected from B(Ar²), C(Ar²)₂, C(Ar¹Ar²), Si(Ar²)₂, C=C(Ar²)₂ or C=NAr²;
$X^1$ is on each occurrence, identically or differently, X or a divalent bridge selected from B(R¹), C(R¹)₂, Si(R¹)₂, C=C(R¹)₂, C=NR¹, B(Ar¹), C(Ar¹)₂, Si(Ar¹)₂, C=C(Ar¹)₂ or C=NAr¹;
$R^1$ is on each occurrence, identically or differently, H, D, F, Cl, Br, I, CHO, N(Ar¹)₂, C(=O)Ar¹, P(=O)(Ar¹)₂, S(=O)Ar¹, S(=O)₂Ar¹, CR²=CR²Ar¹, CN, NO₂, Si(R²)₃, B(OR²)₂, B(R²)₂, B(N(R²)₂)₂, OSO₂R², a straight-chain alkyl, alkoxy or thioalkoxy group having 1 to 40 C atoms or a straight-chain alkenyl or alkynyl group having 2 to 40 C atoms or a branched or cyclic alkyl, alkenyl, alkynyl, alkoxy or thioalkoxy group having 3 to 40 C atoms, each of which is optionally substituted by one or more radicals R², where one or more, preferably non-adjacent CH₂ groups is optionally replaced by R²C=CR², C≡C, Si(R²)₂, Ge(R²)₂, Sn(R²)₂, C=O, C=S, C=Se, C=NR², P(=O)(R²), SO, SO₂, NR²,O, S or CONR² and where one or more H atoms is optionally replaced by D, F, Cl, Br, I, CN or NO₂, or an aromatic or heteroaromatic ring system having 5 to 60 aromatic ring atoms, which may in each case be substituted by one or more radicals R², or an aryloxy or hetero-aryloxy group having 5 to 60 aromatic ring atoms, which is optionally substituted by one or more radicals R², or an aralkyl or heteroaralkyl group having 5 to 60 aromatic ring atoms, which is optionally substituted by one or more radicals R²; two or more adjacent substituents R¹ here may also form a mono- or polycyclic, aliphatic or aromatic ring system with one another;
$Ar^1$ is on each occurrence, identically or differently, an aromatic or heteroaromatic ring system having 5 to 30 aromatic ring atoms, which is optionally substituted by one or more radicals R²; two radicals Ar¹ which are bonded to the same nitrogen, phosphorus or boron atom may here also be linked to one another by a single bond or a bridge selected from B(R²), C(R²)₂, Si(R²)₂, C=O, C=NR², C=C(R²)₂, O, S, S=O, SO₂, N(R²), P(R²) and P(=O)R²;
$R^2$ is on each occurrence, identically or differently, H, D or an aliphatic, aromatic and/or heteroaromatic organic radical having 1 to 20 C atoms, in which, in addition, H atoms is optionally replaced by D or F; two or more adjacent substituents R² here may also form a mono- or polycyclic, aliphatic or aromatic ring system with one another;
n is 0 or 1;
m is 0, 1,2 or 3;
o is 0, 1, 2, 3 or 4 if m=0 and is 0, 1, 2 or 3 if m=1;
p, q are on each occurrence, identically or differently, 0 or 1, with the proviso that p+q is equal to 1 or 2;
where the compound of the formula (1), (2), (3a) or (3b) contains at least one group Ar², where Ar² is selected from a carbazole group, an azacarbazole group, a cis- or trans-indenocarbazole group, a cis- or trans-indenoazacarbazole group or a cis- or trans-indolocarbazole group, each of which is optionally substituted by one or more radicals R¹, where two or more adjacent substituents R¹, together with the atoms to which they are bonded, may also form a mono- or polycyclic, aliphatic or aromatic ring system with one another, with the proviso that the group Ar²is not in conjugation with the group Ar.

2. The compound according to claim 1, wherein the following applies to the symbols in the compounds of the formulae (1), (2), (3a) and (3b):
Ar is on each occurrence, identically or differently, triazine, pyrimidine or pyrazine, in particular triazine, each of which is optionally substituted by one or more radicals R¹;
X is on each occurrence, identically or differently, a group of the formula (4), where the dashed bond in each case indicates the bond to the two benzene rings;
$X^1$ is, identically or differently on each occurrence, a divalent bridge selected from C(R¹)₂, Si(R¹)₂ or C=C(R¹)₂;
$R^1$ is on each occurrence, identically or differently, H, a straight-chain alkyl, alkoxy or thioalkoxy group having 1 to 8 C atoms or an aromatic or heteroaromatic ring system having 5 to 20 aromatic ring atoms, each of which is optionally substituted by one or more radicals R², or an aryloxy or heteroaryloxy group having 5 to 20 aromatic ring atoms, which is optionally substituted by one or more radicals R², or a combination of these systems; two or more adjacent substituents R¹ here may also form a mono- or polycyclic, aliphatic or aromatic ring system with one another;
$Ar^1$ is on each occurrence, identically or differently, an aromatic or heteroaromatic ring system having 5 to 20, which is optionally substituted by one or more radicals R$^2$; two radicals Ar$^1$ which are bonded to the same nitrogen, phosphorus or boron atom may here also be linked to one another by a single bond or a bridge selected from C(R$^2$)$_2$, C=O, O, S and N(R$^2$);

R$^2$ is on each occurrence, identically or differently, H, D or an aliphatic, aromatic and/or heteroaromatic organic radical having 1 to 10 C atoms, in which, in addition, H atoms is optionally replaced by F; two or more adjacent substituents R$^2$ here may also form a mono- or polycyclic, aliphatic or aromatic ring system with one another;

Ar$^2$ is on each occurrence selected from carbazole, azacarbazole, indenocarbazole and indolocarbazole, each of which may also be substituted by one or more radicals R$^1$;

the other symbols and indices have the meanings indicated in claim 1.

3. The compound according to claim 2, wherein
X$^1$ is C(R$^1$)$_2$;
Ar$^1$ is on each occurrence, identically or differently, an aromatic or heteroaromatic ring system having 5 to 10, aromatic ring atoms, which is optionally substituted by one or more radicals R$^2$; two radicals Ar$^1$ which are bonded to the same nitrogen, phosphorus or boron atom may here also be linked to one another by a single bond or a bridge selected from C(R$^2$)$_2$, C=O, O, S and N(R$^2$);

R$^2$ is on each occurrence, identically or differently, H, D or an aliphatic, aromatic and/or heteroaromatic organic radical having 1 to 6 C atoms, in which, in addition, H atoms is optionally replaced by F; two or more adjacent substituents R$^2$ here may also form a mono- or polycyclic, aliphatic or aromatic ring system with one another.

4. The compound according to claim 1, wherein the compound is selected from compounds of the formulae (5) to (12),

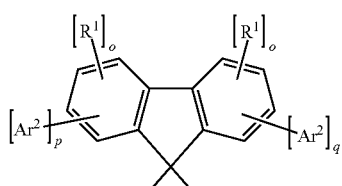

formula (5)

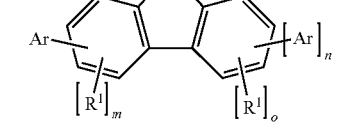

formula (6)

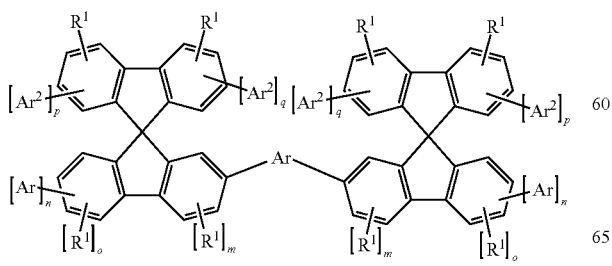

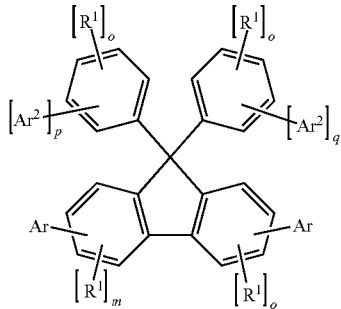

formula (7a)

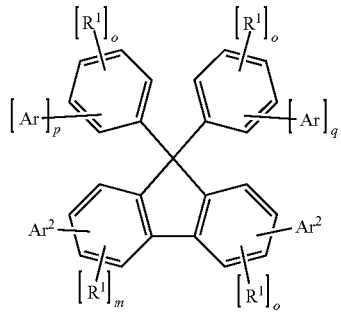

formula (7b)

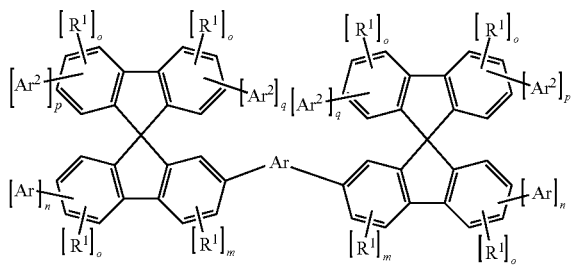

formula (8)

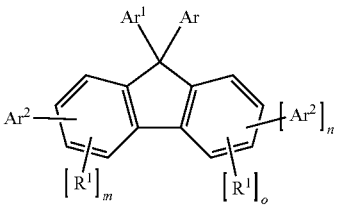

formula (9a)

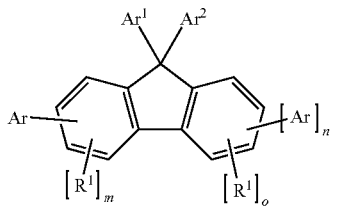

formula (9b)

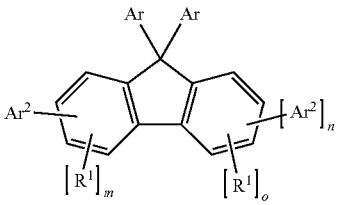

formula (10a)

-continued
formula (10b)
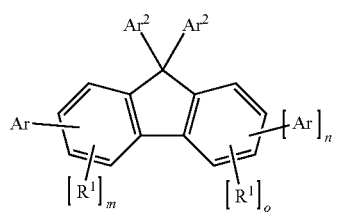
formula (11a)
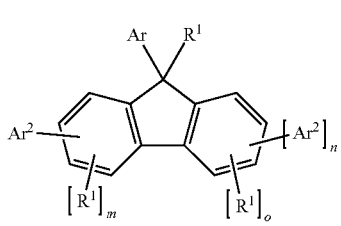
formula (11b)
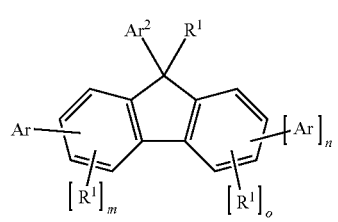
formula (12a)
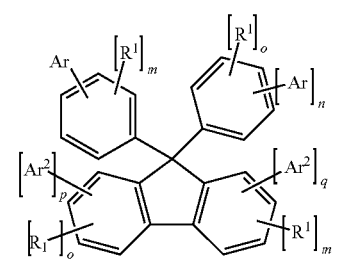
formula (12b)
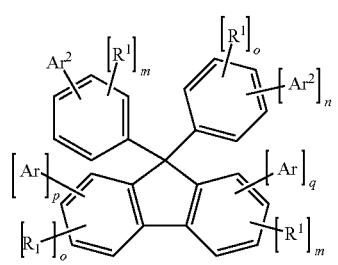
where the symbols and indices have the same meanings as described in claim 1.
5. The compound according to claim 1, wherein the compound is selected from compounds of the formulae (13) to (20),
formula (13)
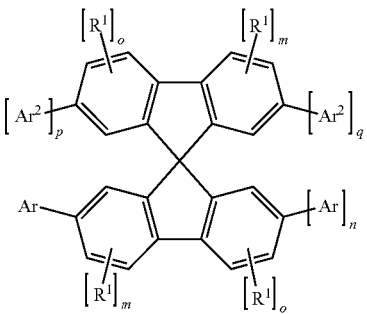
formula (14)
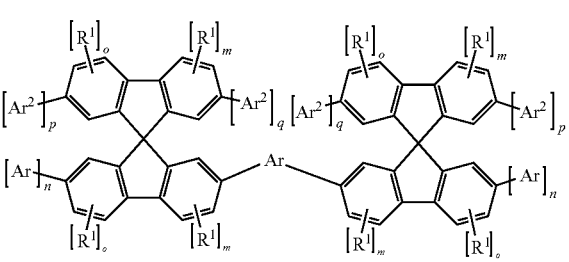
formula (15a)
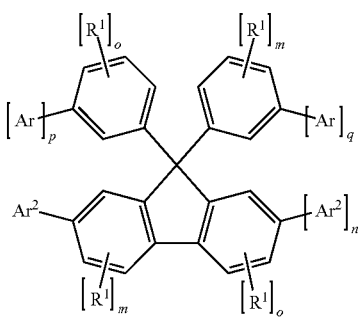
formula (15b)
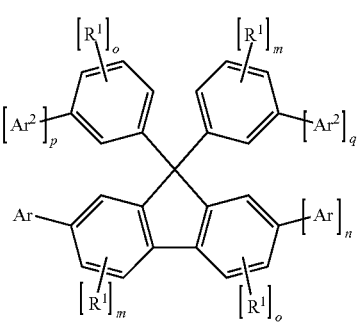
formula (16)
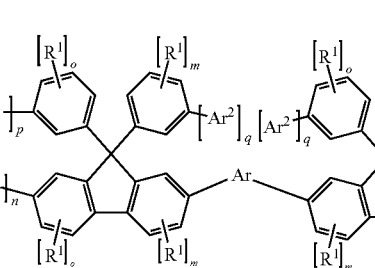

-continued
formula (17a)
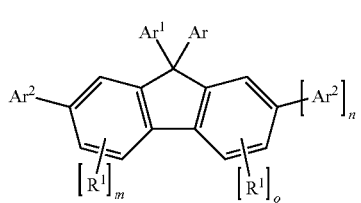
formula (17b)
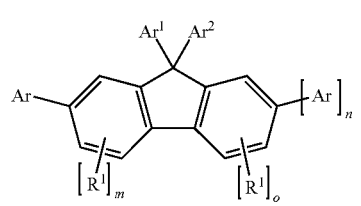
formula (18a)
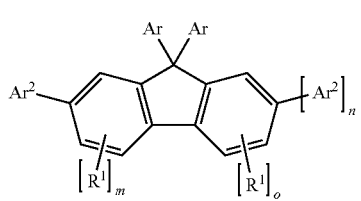
formula (18b)
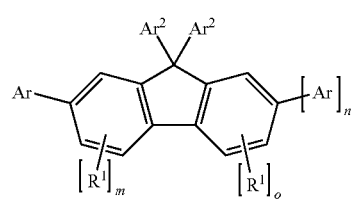
formula (19a)
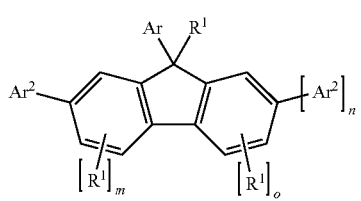
formula (19b)
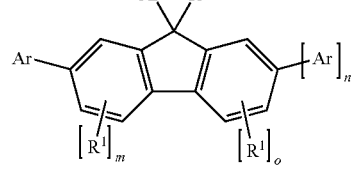
formula (20a)
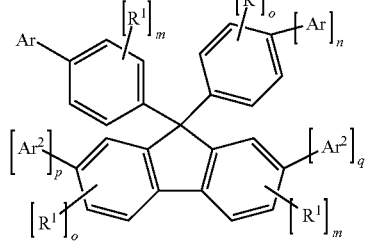
formula (20b)
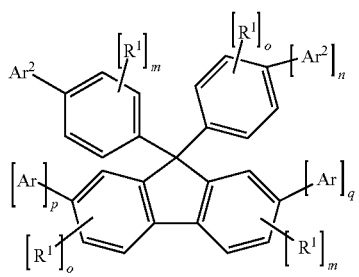
where the symbols and indices have the meanings indicated in claim 1.
6. The compound according to claim 1, wherein the compound is selected from compounds of the formulae (21) to (28),
formula (21)
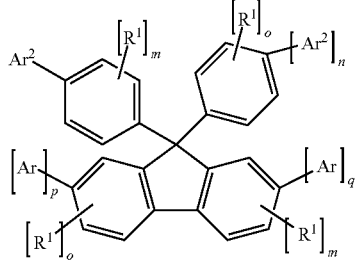
formula (22)
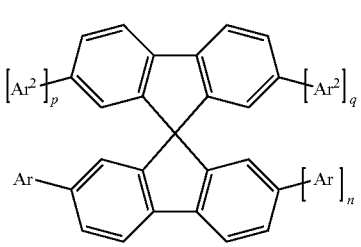
formula (23a)
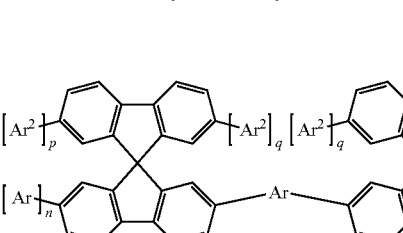
formula (23b)
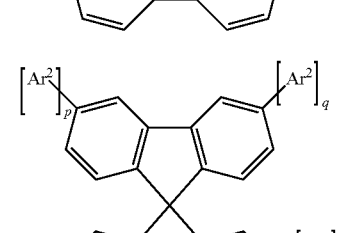

-continued

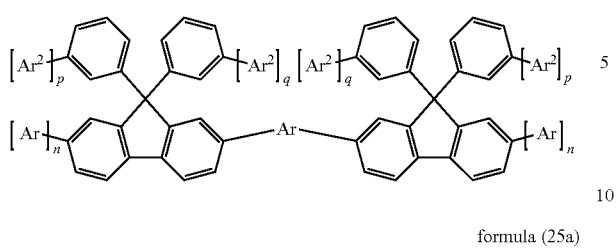
formula (24)

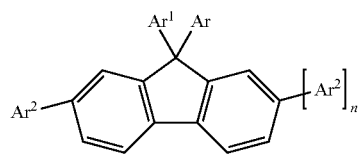
formula (25a)

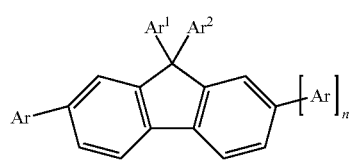
formula (25b)

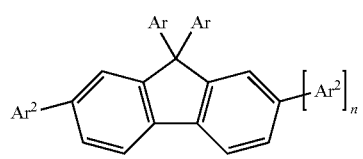
formula (26a)

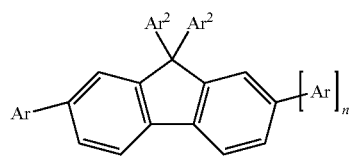
formula (26b)

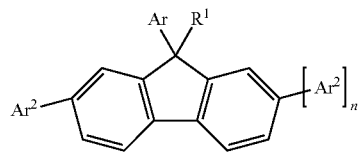
formula (27a)

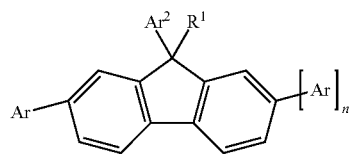
formula (27b)

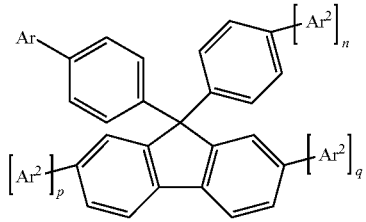
formula (28a)

-continued

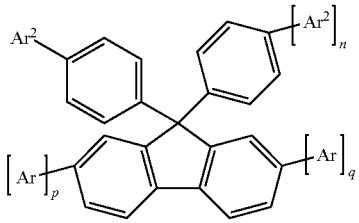
formula (28b)

where the symbols and indices have the meanings indicated above, p and q are on each occurrence, identically or differently, 0 or 1, where the sum of p and q is 1 or 2, and n is 0 or 1.

7. The compound according to claim 1, wherein the monovalent group Ar is selected from the groups of the formulae (29) to (41), where the dashed bond in each case indicates the bond from the group to the fluorene or spirobifluorene or, optionally, to $Ar^1$, and $R^1$ has the same meaning as described in claim 1, and in that the divalent group Ar in compounds of the formula (2) is selected from the groups of the formulae (42) to (49), where the dashed bonds in each case indicate the bond from the group to the fluorene or spirobifluorene, and $R^1$ has the same meaning as described in claim 1:

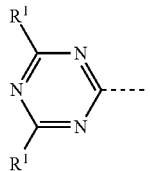
formula (29)

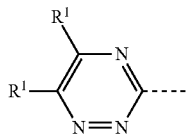
formula (30)

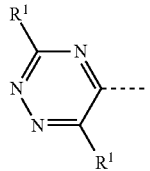
formula (31)

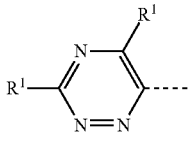
formula (32)

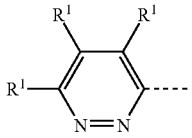
formula (33)

formula (34)
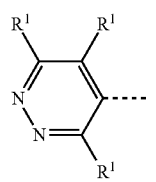

formula (35)
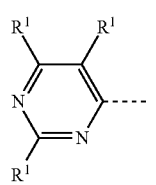

formula (36)
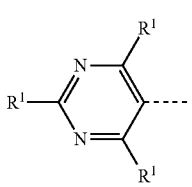

formula (37)
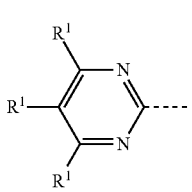

formula (38)
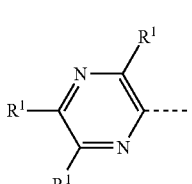

formula (39)
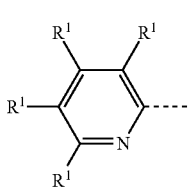

formula (40)
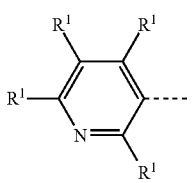

formula (41)
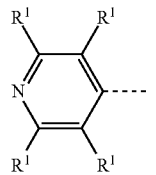

formula (42)
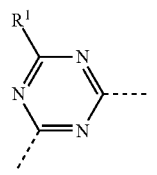

formula (43)
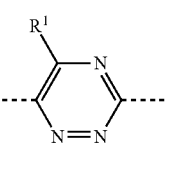

formula (44)
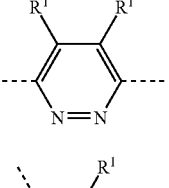

formula (45)
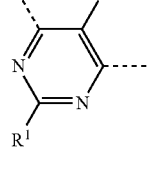

formula (46)
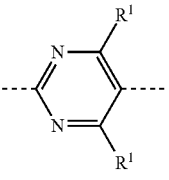

formula (47)
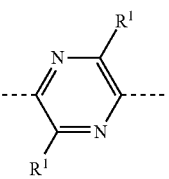

formula (48)
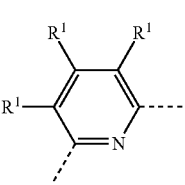

formula (49)
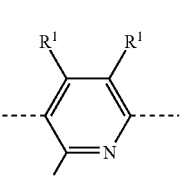

8. The compound according to claim 1, wherein the groups $Ar^2$ are selected from the formulae (50) to (63), where the dashed bond in each case indicates the bonding of this group in the molecule, and the other symbols and indices used have the meanings given in claim 1:

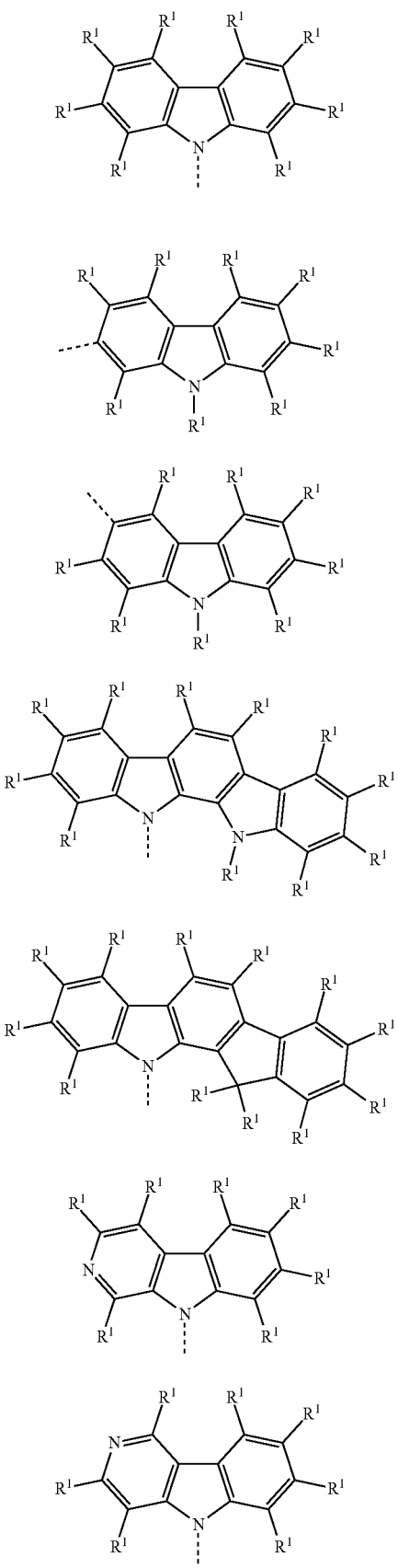
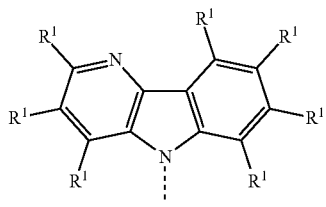
formula (50)
formula (57)
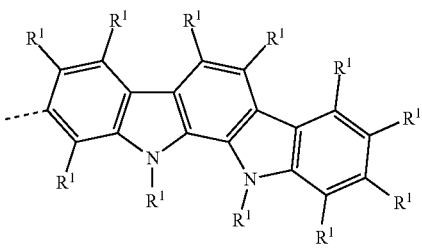
formula (58)
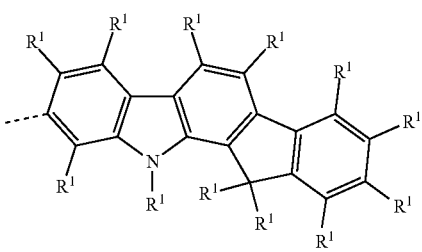
formula (59)
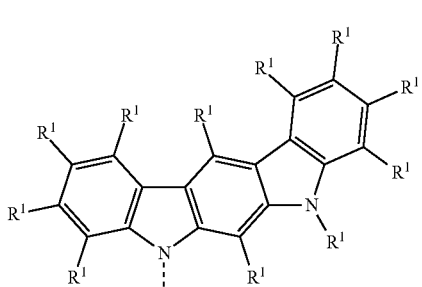
formula (60)
formula (61)
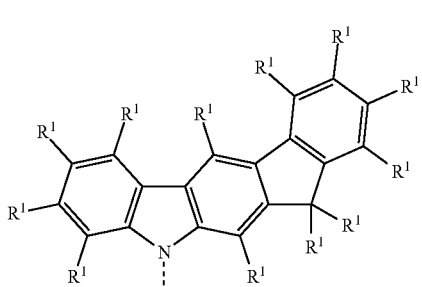
formula (62)
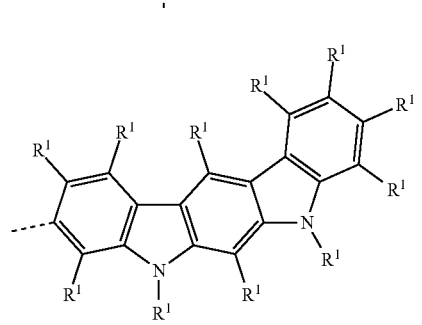

formula (63)

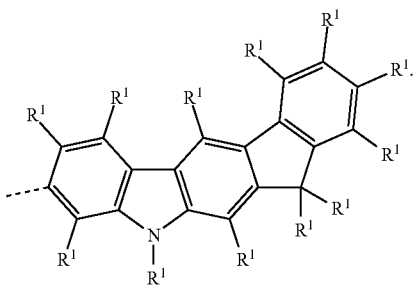

9. A process for the preparation of the compound according to claim 1, which comprises introducing the groups Ar and/or Ar² by a metal-catalysed coupling reaction.

10. A process for the preparation of the compound according to claim 1, which comprises introducing the groups Ar and/or Ar² by a Suzuki coupling or Hartwig-Buchwald coupling.

11. An electronic device which comprises the compound according to claim 1.

12. The electronic device as claimed in claim 11, wherein the device is selected from the group consisting of organic electroluminescent device (OLED, PLED), organic integrated circuit (O—IC), organic field-effect transistor (O-FET), organic thin-film transistor (O-TFT), organic light-emitting transistor (O-LET), organic solar cell (O—SC), organic optical detector, organic photoreceptor, organic field-quench device (O-FQD), light-emitting electrochemical cell (LEC) or organic laser diode (O-laser), and said compound is in at least one layer.

13. An organic electroluminescent device which comprises the compound according to claim 1 is employed in an emission layer.

14. An organic electroluminescent device which comprises the compound according to claim 1 is employed in a matrix material for phosphorescent emitters, or in an electron-transport layer.

15. The organic electroluminescent device according to claim 12, wherein the phosphorescent emitter is a compound of the formulae (64) to (67), formula (64)

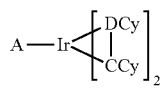

formula (65)

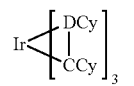

formula (66)

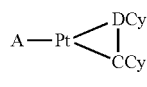

formula (67)

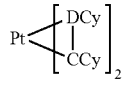

where R¹ has the same meaning as described above, and the following applies to the other symbols used:

DCy is, identically or differently on each occurrence, a cyclic group which contains at least one donor atom, via which the cyclic group is bonded to the metal, and which may in turn carry one or more substituents R¹; the groups DCy and CCy are connected to one another via a covalent bond;

CCy is, identically or differently on each occurrence, a cyclic group which contains a carbon atom via which the cyclic group is bonded to the metal and which may in turn carry one or more substituents R¹;

A is, identically or differently on each occurrence, a monoanionic, bidentate-chelating ligand.

16. The organic electroluminescent device according to claim 15, wherein

DCy is, identically or differently on each occurrence, a cyclic group which contains at least one nitrogen, carbon in the form of a carbene or phosphorus, via which the cyclic group is bonded to the metal, and which may in turn carry one or more substituents R¹; the groups DCy and CCy are connected to one another via a covalent bond;

and

A is, identically or differently on each occurrence, a diketonate ligand.

17. A mixture comprising at least one phosphorescent emitter and at least one compound according to claim 1.

18. A solution or formulation comprising at least one compound according to claim 1 and at least one solvent.

19. A solution or formulation comprising at least one compound according to claim 1 and at least one organic solvent.

20. A solution or formulation comprising said mixture according to claim 17 and at least one solvent.

\* \* \* \* \*